(12) United States Patent
Borovsky et al.

(10) Patent No.: US 6,566,129 B1
(45) Date of Patent: *May 20, 2003

(54) TRANSFORMED CELLS USEFUL FOR THE CONTROL OF PESTS

(75) Inventors: Dov Borovsky, Vero Beach, FL (US); Yaaquov Schlesinger, Vero Beach, FL (US); Sabine Maria Isidore Nauwelaers, Vero Beach, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/551,737

(22) Filed: Apr. 18, 2000

Related U.S. Application Data

(63) Continuation-in-part of application No. 09/295,846, filed on Apr. 21, 1999.

(51) Int. Cl.[7] .......................... C12N 5/00; C07H 21/02; C07H 21/04
(52) U.S. Cl. ...................... 435/325; 536/23.1; 536/23.5
(58) Field of Search .......................... 421/93.21, 93.51; 435/254.2, 255.1, 320.1, 471; 530/325, 300; 536/23.1–23.5; 514/44

(56) References Cited

U.S. PATENT DOCUMENTS

| | | |
|---|---|---|
| 4,714,763 A | 12/1987 | Theodoropulos |
| 5,011,909 A | 4/1991 | Borovsky et al. |
| 5,130,253 A | 7/1992 | Borovsky et al. |
| 5,358,934 A | 10/1994 | Borovsky et al. |
| 5,428,147 A | 6/1995 | Barker et al. |
| 5,439,821 A | 8/1995 | Borovsky et al. |
| 5,459,130 A | 10/1995 | Borovsky et al. |
| 5,501,976 A | 3/1996 | Borovsky et al. |
| 5,629,196 A | 5/1997 | Borovsky et al. |
| 5,753,615 A | 5/1998 | Thorpe et al. |
| 5,792,750 A | 8/1998 | Borovsky et al. |
| 5,849,525 A | 12/1998 | Hediger |

FOREIGN PATENT DOCUMENTS

| | | |
|---|---|---|
| EP | 0 412595 | 2/1991 |
| EP | 0 682115 | 11/1995 |
| EP | 0 018920 | 4/2000 |
| JP | 01 226898 | 9/1989 |
| JP | 07 188282 | 7/1995 |
| WO | 9 321217 | 10/1993 |
| WO | 9 413698 | 6/1994 |

OTHER PUBLICATIONS

Hlavacek et.al.; Synthesis, radiolabeling and biological activity of peptide oostatic hormone and its analogues, 1997, J. Peptide Res. 50: 153–158.*

Eipper et. al.; The Biosynthesi of Neuropeptides: Peptide – Amidation, 1992, Nnnu. Rev. Neurosci. 15: 57–85.*

Rao et al.; Synthesis and expression of genes encoding putative insect neuropeptide precursors in tobacco, 1996, Gene 175: 1–5.*

Menn et. al.; Insect Neuropeptides: Potential New Insect Control Agents, 1989, J. Agric. Food Chem. vol. 37: 271–278.*

Copley et. al.; Expression, processing and secretion of a proteolytically– sensitive insect diuretic . . . found in the secretary pathway, 1998, Biochem. J. 330: 1333–1340.*

Rourke et. al.; Heterologous Expression of Human Cholecystokinin in *Saccharomyces cerevisiae*, 1997, The Journal of Biological Chemistry, vol. 272: 9720–9727.*

Borovsky et al. (1992) "Development of specific RIA and ELISA to study trypsin modulating oostatic factor in mosquitoes" *Archives of Insect Biochemistry and Physiology*, vol. 21(1):13–21.

Shibnev et al. (Jun. 23, 1969) "Synthesis of monomers that are triplets of the "crystalline" part of the collagen molecule" *Chemical Abstracts* 70(25):392–397, abstract only.

Deslauriers et al. (1979) "Steric Effects of Cis–Trans Isomerism on Neighboring Residues in Proline Oligopeptides: A C–NMR Study of Conformational Heterogeneity in Linear Tripeptides" *Biopolymers* 18(3):523–538.

Bordusa, Frank and Hans–Dieter Jakubke (1998) "The Specificity of Prolyl Endopeptidase from *Flavobacterium meningoseptum*: Mapping the S' Subsites by Positional Scanning via Acyl Transfer" *Bioorganic & Medicinal Chemistry* 6:1775–1780.

Kolaskar, A.S. and V. Ramabrahmam (1983) "Conformational properties of pairs of amino acids" *Int. J. Peptide Protein Res.* 22:83–91.

Veenstra, J.A., H.M. Romberg–Privee, H. Schooneveld, J.M. Polak (1985) "Immunocytochemical localization of peptidergic neurons and neurosecretory cells in the neuro–endocrine system of the Colorado potato beetle with antisera to vertebrate regulatory peptides" *Histochemistry* 82:9–18.

Verhaert, Peter, Cornelis J. P. Grimmelikhuijzen, Arnold De Loof (1985) "Distinct Localization of FMRFamide– and Bovine Pancreatic Polypeptide–Like Material in the Brain, Retrocerebral Complex and Suboesophageal Ganglion of the Cockroach *Periplaneta americana* L." *Brain Research* 348:331–338.

(List continued on next page.)

*Primary Examiner*—Deborah Crouch
*Assistant Examiner*—Joseph Woitach
(74) *Attorney, Agent, or Firm*—Saliwanchik, Lloyd & Saliwanchik

(57) ABSTRACT

The subject invention provides materials and methods for the control of pests. Specifically exemplified is the use of recombinant hosts to control mosquito larvae. These hosts, which may be, for example yeast or algae, can be transformed so that they express a pesticidal polypeptide which controls mosquito larvae. These transformed microbes can then be applied to surface waters where mosquito larvae are likely to be found.

22 Claims, 10 Drawing Sheets

OTHER PUBLICATIONS

Borovsky, Dov (1985) "Isolation and Characterization of Highly Purified Mosquito Oostatic Hormone" *Archives of Insect Biochemistry and Physiology* 2:333–349.

Borovsky, Dov (1988) "Oostatic Hormone Inhibits Biosynthesis of Midgut Proteolytic Enzymes and Egg Development in Mosquitoes" *Archives of Insect Biochemistry and Physiology* 7:187–210.

Borosky, Dov (1990) "Mosquito oostatic factor: a novel decapeptide modulating trypsin–like enzyme biosynthesis in the midgut" *The FASEB Journal* 4:3015–3019.

Borovsky, Dov, C.A. Powell, J.K. Nayar, J. Edwin Blalock, T.K. Hayes (1994) "Characterization and localization of mosquito–gut receptors for trypsin modulating oostatic factor using a complementary peptide and immunocytochemistry" *The FASEB Journal* 8:350–355.

Borovsky, Dov, Farida Mahmood (1995) "Feeding the mosquito *Aedes aegypti* with TMOF and its analogs; effect on trypsin biosynthesis and egg development" *Regulatory Peptides* 57:273–281.

Henderson et al. (May 21, 1990) "Physicochemical studies of biologically active peptides by low–temperature reversed phase high–performance liquid chromatography" *Chemical Abstracts*, 112(21), abstract No. 192024, abstract only.

Okada et al. (Nov. 07, 1977) "Synthesis of bradykinin fragments and their effect on pentobarbital sleeping time in mouse" *Chemical Abstracts* 87(19), abstract No. 146142, abstract only.

Curry, W.J., C. Shaw, C.F. Johnston, L. Thim, K.D. Buchanan (1992) "Neuropeptide F: Primary Structure From The Tubellarian, *Artioposthia triangulata*" *Comp. Biochem. Physiol.* 101C(2):269–274.

Leung, P.S., C. Shaw, A.G. Maule, L. Thim, C.F. Johnston, G.B. Irvine (1992) "The primary structure of neuropeptie F (NPF) from the garden snail, *Helix aspersa*" *Regulatory Peptides* 41:71–81.

Maule et al. (1991) "Neuropeptide F: a novel parasitic flatworm regulatory peptide from *Moniezia expansa* (Cestoda: Cyclophyllidea)" *Parasitology* 102:309–316.

Rajpara, Sanjay M., et al. (1992) "Identification and Molecular Cloning of a Neuropeptide Y Homolog That Produces Prolonged Inhibition in Aplysia Neurons" *Neuron* 9:505–513.

Spittaels, Kurt, Peter Verhaert, Christ Shaw, Richard N. Johnston, Bart Devreese, Jos Van Beeumen, Arnold De Loof (1996) "Insect Neuropeptide F (NPF)–related Peptides: Isolation from Colorado Potato Beetle (*Leptinotarsa decemlineata*) Brain" *Insect Biochem. Molec. Biol.* 26(4):375–382.

Borovsky et al. (1991) "Mosquito Oostatic Hormone" *Insect Neuropeptides: Chemistry, Biology Action* 135–142.

Borovsky, Dov, D.A. Carlson, P.R. Griffin, J. Shabanowitz, D.F Hunts (1993) "Mass Spectrometry and Characterization of *Aedes aegypti* Trypsin Modulating Oostatic Factor (TMOF) and its Analogs" *Insect Biochem. Molec. Biol.* 23(6):703–712.

Charbonneau, Harry (1989) "Strategies for Obtaining Partial Amino Acid Sequence Data from Small Quantities (>5 nmol) of Pure or Partially Purified Protein" A Practical Guide to Protein and Peptide Purification for Microsequencing pp. 15–30.

Duve, Hanne, Alan Thorpe, Ray Neville, Norman R. Lazarus (1981) "Isolation and partial characterization of pancreatic polypeptide–like material in the brain of the blowfly *Calliphora vomitoria*" *J. Biochem.* 197:767–770.

Gautheier et al. (1995) "Direct Submission" *Plant Physiol.* 108:1341. (abstract/sequence only).

Hlavacek et al. (Oct. 1998) "The C–Terminus Shortened Analogs of the Insect Peptide Oostatic Hormone with Accelerated Activity" *Bioorg. Chem* 26:131–140.

Ladram et al. (1992) "Characterization of receptors for thyrotropin–releasing hormone–receptors potentiating peptide on rat anterior pituitary membranes" *J. Biol. Chem.* 267(36):25697–25702.

Merkler et al. (1994) "C–Terminal amidated peptides: Production by the in vitro enzymatic amidation of glycine–extended peptides and the importance of the amide to bioactivity" *Enzyme* 16(6):450–456.

Narberhaus et al. (1996) "The *Bradyrhizobium japonicum* rpoH1 gene encoding a sigma 32–likeprotein is part of a unique heat shock gene cluster together with groESL1 and three small heat shock genes" *J. Bacteriol.* 178:5337–5346 (abstract/sequence only).

Pauletti et al. (1996) "Structural requirements for intestinal abosrption of peptide drugs" *J. Controled Rel.* 41:3–17.

Rayne, R.C., M. O'Shea (1992) "Inactivation of Neuropeptide Hormones (AKH I and AKH II) Studied In Vivo and In Vitro" Insect Biochem. Molec. Biol. 22(1):25–34.

Rudinger (Jun. 1976) "Characteristics of the amino acids as components of a peptide hormone sequence" pp 1–7, In Peptide Hormones, Parsons (ed.), University Park press, Baltimore.

Schwartz, J.–C. et al. (1981) "Biological Inactivation of Enkephalins and the Role of Enkephalin–Dipeptidyl–Carboxypeptidase ("Enkephalinase") as Neuropeptidase" Life Sciences 29:1715–1740.

Sober, H.A. (1968) "Handbook of Biochemistry" The Chemical Rubber Co., Cleveland, Ohio, p. C70.

Tykva, Richard et al. (Jun. 26, 2000) "The fate of an oostatic peptide or its analogs including metabolites in insects Diptera and Orthoptera and its transformation to the next generation" *Chemical Abstracts*, vol. 132(26), abstract No. 345576.

* cited by examiner

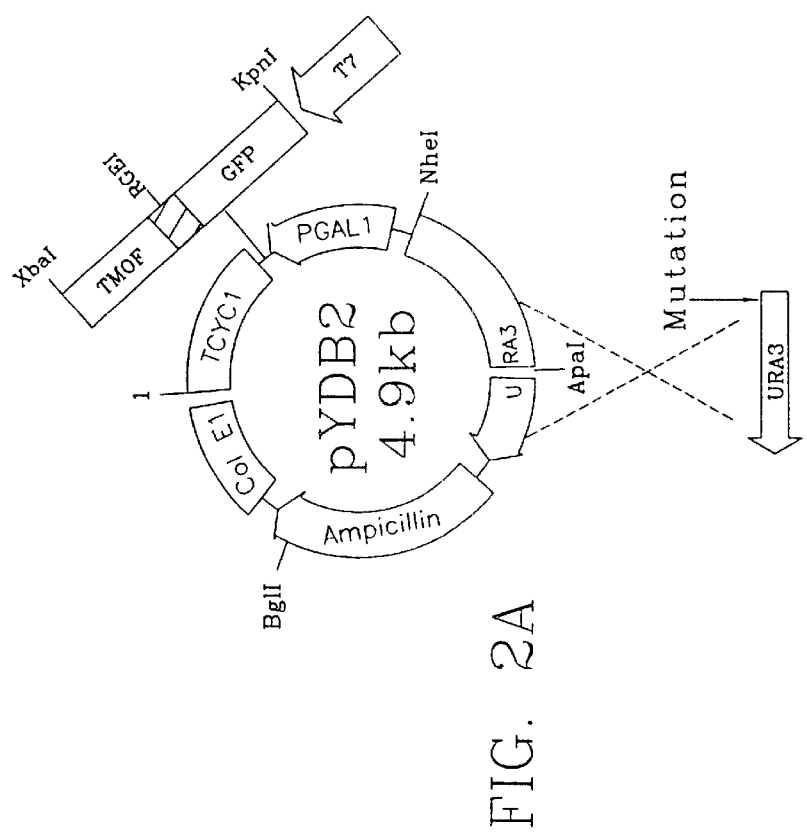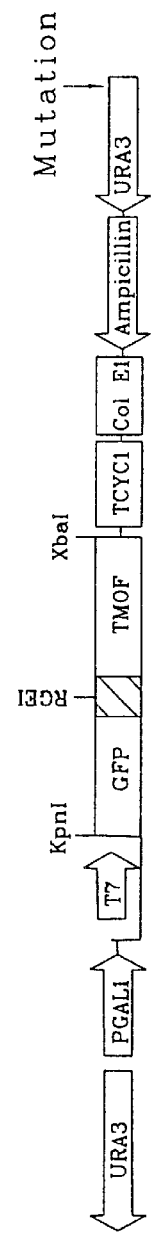
FIG. 2A
FIG. 2B

SEQUENCE LISTING

<160> NUMBER OF SEQ ID NOS: 71

<210> SEQ ID NO 1
<211> LENGTH: 10
<212> TYPE: PRT
<213> ORGANISM: Leptinotarsa decemlineata
<220> FEATURE:
<221> NAME/KEY: MOD_RES
<222> LOCATION: (10)..(10)
<223> OTHER INFORMATION: AMIDATION

<400> SEQUENCE: 1

Ala Arg Gly Pro Gln Leu Arg Leu Arg Phe
1 5 10

<210> SEQ ID NO 2
<211> LENGTH: 8
<212> TYPE: PRT
<213> ORGANISM: Leptinotarsa decemlineata
<220> FEATURE:
<221> NAME/KEY: MOD_RES
<222> LOCATION: (8)..(8)
<223> OTHER INFORMATION: AMIDATION

<400> SEQUENCE: 2

Ala Pro Ser Leu Arg Leu Arg Phe
1 5

<210> SEQ ID NO 3
<211> LENGTH: 378
<212> TYPE: DNA
<213> ORGANISM: Aedes aegypti
<220> FEATURE:
<221> NAME/KEY: CDS
<222> LOCATION: (1)..(189)
<223> OTHER INFORMATION:

<400> SEQUENCE: 3 ata ctg ggg agg ggg ggg ggg gac att ggg tta ctc agt tca gac caa 48
Ile Leu Gly Arg Gly Gly Gly Asp Ile Gly Leu Leu Ser Ser Asp Gln
1 5 10 15 agg agt ttc agc act gaa act ctg ctt aaa gaa cta aaa aga gaa gcg 96
Arg Ser Phe Ser Thr Glu Thr Leu Leu Lys Glu Leu Lys Arg Glu Ala
20 25 30 gcg gct gag gag cgg agt gct gcc tcc aac tcg ggg tcg gtg gtt ccc 144
Ala Ala Glu Glu Arg Ser Ala Ala Ser Asn Ser Gly Ser Val Val Pro
35 40 45 ctc tcg gag caa agg ctg atg gga cat ctg gcg gcc gcg ctg tga 189
Leu Ser Glu Gln Arg Leu Met Gly His Leu Ala Ala Ala Leu
50 55 60 gccggctttc ctgctgccac tttgggcgcc ttggatggag atcccaattg cagtttgtat 249 tttatttttt tataagggac acgtggaaaa accaaaccaa accaaacaaa gccaacaaac 309 cacgacggtc cttattttaa acctcagact ccataaagaa acctttctat ccaaaaaaaa 369 aaaaaaaaa                                                              378

<210> SEQ ID NO 4
<211> LENGTH: 62
<212> TYPE: PRT
<213> ORGANISM: Aedes aegypti

<400> SEQUENCE: 4

Ile Leu Gly Arg Gly Gly Gly Asp Ile Gly Leu Leu Ser Ser Asp Gln
1               5                   10                  15

Arg Ser Phe Ser Thr Glu Thr Leu Leu Lys Glu Leu Lys Arg Glu Ala
            20                  25                  30

Ala Ala Glu Glu Arg Ser Ala Ala Ser Asn Ser Gly Ser Val Val Pro
        35                  40                  45

Leu Ser Glu Gln Arg Leu Met Gly His Leu Ala Ala Ala Leu
    50                  55                  60

<210> SEQ ID NO 5
<211> LENGTH: 29
<212> TYPE: DNA
<213> ORGANISM: Artificial Sequence
<220> FEATURE:
<223> OTHER INFORMATION: Forward Primer (DB207)

<400> SEQUENCE: 5
aaggtaccat ggctagcaaa ggagaagaa                                         29

<210> SEQ ID NO 6
<211> LENGTH: 71
<212> TYPE: DNA
<213> ORGANISM: Artificial Sequence
<220> FEATURE:
<223> OTHER INFORMATION: Backward Primer (DB209)

<400> SEQUENCE: 6
tttctagatc aaggaggagg aggaggaggt gctggatcat atctaccttc gattttgtag        60
agctcatcca t                                                            71

<210> SEQ ID NO 7
<211> LENGTH: 10
<212> TYPE: DNA
<213> ORGANISM: Artificial Sequence
<220> FEATURE:
<223> OTHER INFORMATION: Oligonucleotide (DB 208)

<400> SEQUENCE: 7
tcgagggtac                                                              10

<210> SEQ ID NO 8
<211> LENGTH: 10
<212> TYPE: PRT
<213> ORGANISM: Artificial Sequence
<220> FEATURE:
<223> OTHER INFORMATION: TMOF peptide
<221> NAME/KEY: MISC_FEATURE
<222> LOCATION: (1)..(1)
<223> OTHER INFORMATION: Can be Ala, Asp, Phe, Gly, Met, Pro, Ser, or
      Tyr.
<221> NAME/KEY: MISC_FEATURE
<222> LOCATION: (2)..(2)
<223> OTHER INFORMATION: Can be Ala, Asp, Glu, Phe, Gly, Asn, Pro, Ser,
      or Tyr.
<221> NAME/KEY: MISC_FEATURE
<222> LOCATION: (3)..(3)
<223> OTHER INFORMATION: Can be Ala, Asp, Arg, Phe, Gly, Leu, Pro, Ser,
      or Tyr.

```
<221> NAME/KEY: MISC_FEATURE
<222> LOCATION: (4)..(4)
<223> OTHER INFORMATION: Is optionally present and can be Ala, Arg, Phe,
      Gly, Leu, or Tyr.
<221> NAME/KEY: MISC_FEATURE
<222> LOCATION: (5)..(5)
<223> OTHER INFORMATION: Is optionally present and can be Ala, Arg, Phe,
      Leu, or Pro.
<221> NAME/KEY: MISC_FEATURE
<222> LOCATION: (6)..(10)
<223> OTHER INFORMATION: Each of amino acids 6-10 are optionally
      present.

<400> SEQUENCE: 8

Xaa Xaa Xaa Xaa Xaa Pro Pro Pro Pro Pro
1               5                   10

<210> SEQ ID NO 9
<211> LENGTH: 4
<212> TYPE: PRT
<213> ORGANISM: Artificial Sequence
<220> FEATURE:
<223> OTHER INFORMATION: Flanking region

<400> SEQUENCE: 9

Pro Pro Pro Pro
1

<210> SEQ ID NO 10
<211> LENGTH: 5
<212> TYPE: PRT
<213> ORGANISM: Artificial Sequence
<220> FEATURE:
<223> OTHER INFORMATION: Flanking region

<400> SEQUENCE: 10

Pro Pro Pro Pro Pro
1               5

<210> SEQ ID NO 11
<211> LENGTH: 10
<212> TYPE: PRT
<213> ORGANISM: Aedes aegypti

<400> SEQUENCE: 11

Tyr Asp Pro Ala Pro Pro Pro Pro Pro Pro
1               5                   10

<210> SEQ ID NO 12
<211> LENGTH: 10
<212> TYPE: PRT
<213> ORGANISM: Artificial Sequence
<220> FEATURE:
<223> OTHER INFORMATION: TMOF peptide

<400> SEQUENCE: 12

Asp Tyr Pro Ala Pro Pro Pro Pro Pro
1               5                   10

<210> SEQ ID NO 13
<211> LENGTH: 8
<212> TYPE: PRT
<213> ORGANISM: Artificial Sequence
<220> FEATURE:
<223> OTHER INFORMATION: TMOF peptide

<400> SEQUENCE: 13

Pro Ala Pro Pro Pro Pro Pro Pro
```

```
<210> SEQ ID NO 14
<211> LENGTH: 5
<212> TYPE: PRT
<213> ORGANISM: Artificial Sequence
<220> FEATURE:
<223> OTHER INFORMATION: TMOF peptide

<400> SEQUENCE: 14

Tyr Asp Pro Ala Pro
1               5

<210> SEQ ID NO 15
<211> LENGTH: 6
<212> TYPE: PRT
<213> ORGANISM: Artificial Sequence
<220> FEATURE:
<223> OTHER INFORMATION: TMOF peptide

<400> SEQUENCE: 15

Tyr Asp Pro Ala Pro Pro
1               5

<210> SEQ ID NO 16
<211> LENGTH: 7
<212> TYPE: PRT
<213> ORGANISM: Artificial Sequence
<220> FEATURE:
<223> OTHER INFORMATION: TMOF peptide

<400> SEQUENCE: 16

Tyr Asp Pro Ala Pro Pro Pro
1               5

<210> SEQ ID NO 17
<211> LENGTH: 8
<212> TYPE: PRT
<213> ORGANISM: Artificial Sequence
<220> FEATURE:
<223> OTHER INFORMATION: TMOF peptide

<400> SEQUENCE: 17

Tyr Asp Pro Ala Pro Pro Pro Pro
1               5

<210> SEQ ID NO 18
<211> LENGTH: 6
<212> TYPE: PRT
<213> ORGANISM: Artificial Sequence
<220> FEATURE:
<223> OTHER INFORMATION: TMOF peptide

<400> SEQUENCE: 18

Asn Pro Thr Asn Leu His
1               5

<210> SEQ ID NO 19
<211> LENGTH: 3
<212> TYPE: PRT
<213> ORGANISM: Artificial Sequence
<220> FEATURE:
<223> OTHER INFORMATION: TMOF peptide

<400> SEQUENCE: 19

Ala Ala Pro
1
```

```
<210> SEQ ID NO 20
<211> LENGTH: 3
<212> TYPE: PRT
<213> ORGANISM: Artificial Sequence
<220> FEATURE:
<223> OTHER INFORMATION: TMOF peptide

<400> SEQUENCE: 20

Ala Asp Pro
1

<210> SEQ ID NO 21
<211> LENGTH: 5
<212> TYPE: PRT
<213> ORGANISM: Artificial Sequence
<220> FEATURE:
<223> OTHER INFORMATION: TMOF peptide

<400> SEQUENCE: 21

Ala Asp Pro Ala Pro
1               5

<210> SEQ ID NO 22
<211> LENGTH: 3
<212> TYPE: PRT
<213> ORGANISM: Artificial Sequence
<220> FEATURE:
<223> OTHER INFORMATION: TMOF peptide

<400> SEQUENCE: 22

Ala Pro Ala
1

<210> SEQ ID NO 23
<211> LENGTH: 3
<212> TYPE: PRT
<213> ORGANISM: Artificial Sequence
<220> FEATURE:
<223> OTHER INFORMATION: TMOF peptide

<400> SEQUENCE: 23

Asp Ala Ala
1

<210> SEQ ID NO 24
<211> LENGTH: 2
<212> TYPE: PRT
<213> ORGANISM: Artificial Sequence
<220> FEATURE:
<223> OTHER INFORMATION: TMOF peptide

<400> SEQUENCE: 24

Asp Phe
1

<210> SEQ ID NO 25
<211> LENGTH: 3
<212> TYPE: PRT
<213> ORGANISM: Artificial Sequence
<220> FEATURE:
<223> OTHER INFORMATION: TMOF peptide

<400> SEQUENCE: 25

Asp Pro Ala
1
```

```
<210> SEQ ID NO 26
<211> LENGTH: 2
<212> TYPE: PRT
<213> ORGANISM: Artificial Sequence
<220> FEATURE:
<223> OTHER INFORMATION: TMOF peptide

<400> SEQUENCE: 26

Asp Tyr
1

<210> SEQ ID NO 27
<211> LENGTH: 3
<212> TYPE: PRT
<213> ORGANISM: Artificial Sequence
<220> FEATURE:
<223> OTHER INFORMATION: TMOF peptide

<400> SEQUENCE: 27

Asp Tyr Pro
1

<210> SEQ ID NO 28
<211> LENGTH: 3
<212> TYPE: PRT
<213> ORGANISM: Artificial Sequence
<220> FEATURE:
<223> OTHER INFORMATION: TMOF peptide

<400> SEQUENCE: 28

Phe Ala Pro
1

<210> SEQ ID NO 29
<211> LENGTH: 3
<212> TYPE: PRT
<213> ORGANISM: Artificial Sequence
<220> FEATURE:
<223> OTHER INFORMATION: TMOF peptide

<400> SEQUENCE: 29

Phe Asp Pro
1

<210> SEQ ID NO 30
<211> LENGTH: 5
<212> TYPE: PRT
<213> ORGANISM: Artificial Sequence
<220> FEATURE:
<223> OTHER INFORMATION: TMOF peptide

<400> SEQUENCE: 30

Phe Asp Pro Ala Pro
1               5

<210> SEQ ID NO 31
<211> LENGTH: 3
<212> TYPE: PRT
<213> ORGANISM: Artificial Sequence
<220> FEATURE:
<223> OTHER INFORMATION: TMOF peptide

<400> SEQUENCE: 31

Phe Ser Pro
1
```

<210> SEQ ID NO 32
<211> LENGTH: 9
<212> TYPE: PRT
<213> ORGANISM: Artificial Sequence
<220> FEATURE:
<223> OTHER INFORMATION: TMOF peptide

<400> SEQUENCE: 32

Met Pro Asp Tyr Pro Pro Pro Pro Pro
1               5

<210> SEQ ID NO 33
<211> LENGTH: 3
<212> TYPE: PRT
<213> ORGANISM: Artificial Sequence
<220> FEATURE:
<223> OTHER INFORMATION: TMOF peptide

<400> SEQUENCE: 33

Pro Ala Ala
1

<210> SEQ ID NO 34
<211> LENGTH: 3
<212> TYPE: PRT
<213> ORGANISM: Artificial Sequence
<220> FEATURE:
<223> OTHER INFORMATION: TMOF peptide

<400> SEQUENCE: 34

Pro Ala Pro
1

<210> SEQ ID NO 35
<211> LENGTH: 3
<212> TYPE: PRT
<213> ORGANISM: Artificial Sequence
<220> FEATURE:
<223> OTHER INFORMATION: TMOF peptide
<221> NAME/KEY: MISC_FEATURE
<222> LOCATION: (2)..(2)
<223> OTHER INFORMATION: Dextrorotary Asp

<400> SEQUENCE: 35

Tyr Xaa Pro
1

<210> SEQ ID NO 36
<211> LENGTH: 5
<212> TYPE: PRT
<213> ORGANISM: Artificial Sequence
<220> FEATURE:
<223> OTHER INFORMATION: TMOF peptide
<221> NAME/KEY: MISC_FEATURE
<222> LOCATION: (2)..(2)
<223> OTHER INFORMATION: Dextrorotary Asp

<400> SEQUENCE: 36

Tyr Xaa Pro Ala Pro
1               5

<210> SEQ ID NO 37
<211> LENGTH: 3
<212> TYPE: PRT
<213> ORGANISM: Artificial Sequence
<220> FEATURE:
<223> OTHER INFORMATION: TMOF peptide

<400> SEQUENCE: 37

Tyr Ala Pro
1

<210> SEQ ID NO 38
<211> LENGTH: 2
<212> TYPE: PRT
<213> ORGANISM: Artificial Sequence
<220> FEATURE:
<223> OTHER INFORMATION: TMOF peptide

<400> SEQUENCE: 38

Tyr Asp
1

<210> SEQ ID NO 39
<211> LENGTH: 3
<212> TYPE: PRT
<213> ORGANISM: Artificial Sequence
<220> FEATURE:
<223> OTHER INFORMATION: TMOF peptide

<400> SEQUENCE: 39

Tyr Asp Ala
1

<210> SEQ ID NO 40
<211> LENGTH: 5
<212> TYPE: PRT
<213> ORGANISM: Artificial Sequence
<220> FEATURE:
<223> OTHER INFORMATION: TMOF peptide

<400> SEQUENCE: 40

Tyr Asp Ala Ala Pro
1               5

<210> SEQ ID NO 41
<211> LENGTH: 3
<212> TYPE: PRT
<213> ORGANISM: Artificial Sequence
<220> FEATURE:
<223> OTHER INFORMATION: TMOF peptide

<400> SEQUENCE: 41

Tyr Asp Phe
1

<210> SEQ ID NO 42
<211> LENGTH: 5
<212> TYPE: PRT
<213> ORGANISM: Artificial Sequence
<220> FEATURE:
<223> OTHER INFORMATION: TMOF peptide

<400> SEQUENCE: 42

Tyr Asp Phe Ala Pro
1               5

<210> SEQ ID NO 43
<211> LENGTH: 3
<212> TYPE: PRT
<213> ORGANISM: Artificial Sequence
<220> FEATURE:
<223> OTHER INFORMATION: TMOF peptide

<400> SEQUENCE: 43

Tyr Asp Gly
1

<210> SEQ ID NO 44
<211> LENGTH: 5
<212> TYPE: PRT
<213> ORGANISM: Artificial Sequence
<220> FEATURE:
<223> OTHER INFORMATION: TMOF peptide

<400> SEQUENCE: 44

Tyr Asp Leu Ala Pro
1               5

<210> SEQ ID NO 45
<211> LENGTH: 3
<212> TYPE: PRT
<213> ORGANISM: Artificial Sequence
<220> FEATURE:
<223> OTHER INFORMATION: TMOF peptide

<400> SEQUENCE: 45

Tyr Asp Pro
1

<210> SEQ ID NO 46
<211> LENGTH: 3
<212> TYPE: PRT
<213> ORGANISM: Artificial Sequence
<220> FEATURE:
<223> OTHER INFORMATION: TMOF peptide
<221> NAME/KEY: MISC_FEATURE
<222> LOCATION: (1)..(1)
<223> OTHER INFORMATION: Dextrorotary Tyr

<400> SEQUENCE: 46

Xaa Asp Pro
1

<210> SEQ ID NO 47
<211> LENGTH: 5
<212> TYPE: PRT
<213> ORGANISM: Artificial Sequence
<220> FEATURE:
<223> OTHER INFORMATION: TMOF peptide

<400> SEQUENCE: 47

Tyr Asp Pro Ala Phe
1               5

<210> SEQ ID NO 48
<211> LENGTH: 5
<212> TYPE: PRT
<213> ORGANISM: Artificial Sequence
<220> FEATURE:
<223> OTHER INFORMATION: TMOF peptide

<400> SEQUENCE: 48

Tyr Asp Pro Ala Leu
1               5

<210> SEQ ID NO 49
<211> LENGTH: 5
<212> TYPE: PRT
<213> ORGANISM: Artificial Sequence
<220> FEATURE:
<223> OTHER INFORMATION: TMOF peptide
<221> NAME/KEY: MISC_FEATURE

```
<222> LOCATION: (1)..(1)
<223> OTHER INFORMATION: Dextrorotary Tyr

<400> SEQUENCE: 49

Xaa Asp Pro Ala Pro
1               5

<210> SEQ ID NO 50
<211> LENGTH: 5
<212> TYPE: PRT
<213> ORGANISM: Artificial Sequence
<220> FEATURE:
<223> OTHER INFORMATION: TMOF peptide

<400> SEQUENCE: 50

Tyr Asp Pro Phe Pro
1               5

<210> SEQ ID NO 51
<211> LENGTH: 5
<212> TYPE: PRT
<213> ORGANISM: Artificial Sequence
<220> FEATURE:
<223> OTHER INFORMATION: TMOF peptide

<400> SEQUENCE: 51

Tyr Asp Pro Gly Pro
1               5

<210> SEQ ID NO 52
<211> LENGTH: 5
<212> TYPE: PRT
<213> ORGANISM: Artificial Sequence
<220> FEATURE:
<223> OTHER INFORMATION: TMOF peptide

<400> SEQUENCE: 52

Tyr Asp Pro Leu Pro
1               5

<210> SEQ ID NO 53
<211> LENGTH: 5
<212> TYPE: PRT
<213> ORGANISM: Artificial Sequence
<220> FEATURE:
<223> OTHER INFORMATION: TMOF peptide

<400> SEQUENCE: 53

Tyr Glu Pro Ala Pro
1               5

<210> SEQ ID NO 54
<211> LENGTH: 5
<212> TYPE: PRT
<213> ORGANISM: Artificial Sequence
<220> FEATURE:
<223> OTHER INFORMATION: TMOF peptide

<400> SEQUENCE: 54

Tyr Phe Pro Ala Pro
1               5

<210> SEQ ID NO 55
<211> LENGTH: 5
<212> TYPE: PRT
<213> ORGANISM: Artificial Sequence
<220> FEATURE:
```

-continued

<223> OTHER INFORMATION: TMOF peptide

<400> SEQUENCE: 55

Tyr Asn Pro Ala Pro
1               5

<210> SEQ ID NO 56
<211> LENGTH: 3
<212> TYPE: PRT
<213> ORGANISM: Artificial Sequence
<220> FEATURE:
<223> OTHER INFORMATION: TMOF peptide

<400> SEQUENCE: 56

Tyr Ser Phe
1

<210> SEQ ID NO 57
<211> LENGTH: 5
<212> TYPE: PRT
<213> ORGANISM: Artificial Sequence
<220> FEATURE:
<223> OTHER INFORMATION: TMOF peptide

<400> SEQUENCE: 57

Tyr Ala Pro Ala Pro
1               5

<210> SEQ ID NO 58
<211> LENGTH: 5
<212> TYPE: PRT
<213> ORGANISM: Artificial Sequence
<220> FEATURE:
<223> OTHER INFORMATION: TMOF peptide

<400> SEQUENCE: 58

Tyr Ser Pro Ala Pro
1               5

<210> SEQ ID NO 59
<211> LENGTH: 5
<212> TYPE: PRT
<213> ORGANISM: Artificial Sequence
<220> FEATURE:
<223> OTHER INFORMATION: TMOF peptide

<400> SEQUENCE: 59

Tyr Asp Pro Ala Ala
1               5

<210> SEQ ID NO 60
<211> LENGTH: 4
<212> TYPE: PRT
<213> ORGANISM: Artificial Sequence
<220> FEATURE:
<223> OTHER INFORMATION: TMOF-R analogue peptide

<400> SEQUENCE: 60

Asp Pro Ala Arg
1

<210> SEQ ID NO 61
<211> LENGTH: 16
<212> TYPE: PRT
<213> ORGANISM: Artificial Sequence
<220> FEATURE:
<223> OTHER INFORMATION: TMOF-R analogue peptide

```
<400> SEQUENCE: 61

Asp Pro Ala Arg Asp Pro Ala Arg Asp Pro Ala Arg Asp Pro Ala Arg
1               5                   10                  15

<210> SEQ ID NO 62
<211> LENGTH: 2
<212> TYPE: PRT
<213> ORGANISM: Artificial Sequence
<220> FEATURE:
<223> OTHER INFORMATION: TMOF peptide
<221> NAME/KEY: MISC_FEATURE
<222> LOCATION: (1)..(1)
<223> OTHER INFORMATION: Can be Ala, Asp, Phe, Met or Tyr.
<221> NAME/KEY: MISC_FEATURE
<222> LOCATION: (2)..(2)
<223> OTHER INFORMATION: Can be Ala, Asp, Glu, Pro, or Tyr.

<400> SEQUENCE: 62

Xaa Xaa
1

<210> SEQ ID NO 63
<211> LENGTH: 10
<212> TYPE: PRT
<213> ORGANISM: Artificial Sequence
<220> FEATURE:
<223> OTHER INFORMATION: Unamidated version of NPF I

<400> SEQUENCE: 63

Ala Arg Gly Pro Gln Leu Arg Leu Arg Phe
1               5                   10

<210> SEQ ID NO 64
<211> LENGTH: 8
<212> TYPE: PRT
<213> ORGANISM: Artificial Sequence
<220> FEATURE:
<223> OTHER INFORMATION: Unamidated version of NPF II

<400> SEQUENCE: 64

Ala Pro Ser Leu Arg Leu Arg Phe
1               5

<210> SEQ ID NO 65
<211> LENGTH: 42
<212> TYPE: DNA
<213> ORGANISM: Artificial Sequence
<220> FEATURE:
<223> OTHER INFORMATION: TMOF synthetic gene sense strand

<400> SEQUENCE: 65
tcgagatgta tgatccagca cctcctcctc ctcctccttg at                          42

<210> SEQ ID NO 66
<211> LENGTH: 42
<212> TYPE: DNA
<213> ORGANISM: Artificial Sequence
<220> FEATURE:
<223> OTHER INFORMATION: TMOF synthetic gene antisense strand

<400> SEQUENCE: 66
ctagatcaag gaggaggagg aggaggtgct ggatcataca tc                          42

<210> SEQ ID NO 67
<211> LENGTH: 11
<212> TYPE: PRT
```

```
<213> ORGANISM: Artificial Sequence
<220> FEATURE:
<223> OTHER INFORMATION: TMOF-R analogue peptide

<400> SEQUENCE: 67

Tyr Asp Pro Ala Pro Pro Pro Pro Pro Arg
1               5                   10

<210> SEQ ID NO 68
<211> LENGTH: 6
<212> TYPE: PRT
<213> ORGANISM: Artificial Sequence
<220> FEATURE:
<223> OTHER INFORMATION: TMOF-R analogue peptide

<400> SEQUENCE: 68

Tyr Asp Pro Ala Pro Arg
1               5

<210> SEQ ID NO 69
<211> LENGTH: 6
<212> TYPE: PRT
<213> ORGANISM: Artificial Sequence
<220> FEATURE:
<223> OTHER INFORMATION: TMOF-R analogue peptide

<400> SEQUENCE: 69

Tyr Asp Pro Ala Phe Arg
1               5

<210> SEQ ID NO 70
<211> LENGTH: 5
<212> TYPE: PRT
<213> ORGANISM: Artificial Sequence
<220> FEATURE:
<223> OTHER INFORMATION: TMOF-R analogue peptide

<400> SEQUENCE: 70

Tyr Asp Pro Ala Arg
1               5

<210> SEQ ID NO 71
<211> LENGTH: 4
<212> TYPE: PRT
<213> ORGANISM: Artificial Sequence
<220> FEATURE:
<223> OTHER INFORMATION: TMOF-R analogue peptide

<400> SEQUENCE: 71

Tyr Asp Pro Arg
1
```

TRANSFORMED CELLS USEFUL FOR THE CONTROL OF PESTS

CROSS-REFERENCE TO RELATED APPLICATION

This application is a continuation-in-part of U.S. patent application Ser. No. 09/295,846, filed on Apr. 21, 1999.

The subject invention was made with government support under research projects supported by NIH Grant No. AI 41254-01 and USDA/FAES/FME-03249. The government has certain rights in this invention.

BACKGROUND OF THE INVENTION

Many blood-ingesting pests are known to feed on humans and animals, and many pests are vectors for pathogenic microorganisms which threaten human and animal health, including commercially important livestock, pets and other animals. Various species of mosquitoes, for example, transmit diseases caused by viruses, and many are vectors for disease-causing nematodes and protozoa. Mosquitoes of the genus Anopheles transmit Plasmodium, the protozoan which causes malaria, a devastating disease which results in approximately 1 million deaths annually. The mosquito species *Aedes aegypti* transmits an arbovirus that causes yellow fever in humans. Other arboviruses transmitted by Aedes species include the causative agents of dengue fever, eastern and western encephalitis, Venezuelan equine encephalitis, St. Louis encephalitis, chikungunya, oroponehe and bunyarnidera. The genus Culex, which includes the common house mosquito *C. pipiens*, is implicated in the transmission of various forms of encephalitis and filarial worms. The common house mosquito also transmits *Wuchereria bancrofti* and *Brugia malayi*, which cause various forms of lymphatic filariasis, including elephantiasis. *Trypanasoma cruzi*, the causative agent of Chagas' disease, is transmitted by various species of blood-ingesting Triatominae bugs. The tsetse fly (Glossina spp.) transmits African trypanosomal diseases of humans and cattle. Many other diseases are transmitted by various blood-ingesting pest species. The order Diptera contains a large number of blood-ingesting and disease-bearing pests, including, for example, mosquitoes, black flies, no-see-ums (punkies), horse flies, deer flies and tsetse flies.

Various pesticides have been employed in efforts to control or eradicate populations of disease-bearing pests, such as disease-bearing blood-ingesting pests. For example, DDT, a chlorinated hydrocarbon, has been used in attempts to eradicate malaria-bearing mosquitoes throughout the world. Other examples of chlorinated hydrocarbons are BHC, lindane, chlorobenzilate, methoxychlor, and the cyclodienes (e.g., aldrin, dieldrin, chlordane, heptachlor, and endrin). The long-term stability of many of these pesticides and their tendency to bioaccumulate render them particularly dangerous to many non-pest organisms.

Another common class of pesticides is the organophosphates, which is perhaps the largest and most versatile class of pesticides. Organophosphates include, for example, parathion, Malathion™, diazinon, naled, methyl parathion, and dichlorvos. Organophosphates are generally much more toxic than the chlorinated hydrocarbons. Their pesticidal effect results from their ability to inhibit the enzyme cholinesterase, an essential enzyme in the functioning of the insect nervous system. However, they also have toxic effects on many animals, including humans.

The carbamates, a relatively new group of pesticides, include such compounds as carbamyl, methomyl, and carbofuran. These compounds are rapidly detoxified and eliminated from animal tissues. Their toxicity is thought to involve a mechanism similar to the mechanism of the organophosphates; consequently, they exhibit similar shortcomings, including animal toxicity.

A major problem in pest control results from the capability of many species to develop pesticide resistance. Resistance results from the selection of naturally-occurring mutants possessing biochemical, physiological or behavioristic factors that enable the pests to tolerate the pesticide. Species of Anopheles mosquitoes, for example, have been known to develop resistance to DDT and dieldrin. DDT substitutes, such as Malathion™, propoxur and fenitrothion are available; however, the cost of these substitutes is much greater than the cost of DDT.

There is clearly a longstanding need in the art for pesticidal compounds that are pest- specific, that reduce or eliminate direct and/or indirect threats to human health posed by presently available pesticides, that are environmentally compatible in the sense that they are biodegradable, and are not toxic to non-pest organisms, and have reduced or no tendency to bioaccummulate.

Many pests, including for example blood-inbibing pests, must consume and digest a proteinaceous meal to acquire sufficient essential amino acids for growth, development and the production of mature eggs. Adult pests, such as adult mosquitoes, need these essential amino acids for the production of vitellogenins by the fat body. These vitellogenins are precursors to yolk proteins which are critical components of oogenesis. Many pests, such as house flies and mosquitoes, produce oostatic hormones that inhibit egg development by inhibiting digestion of the protein meal, and thereby limiting the availability of the essential amino acids necessary for egg development.

Serine esterases such as trypsin and trypsin-like enzymes (collectively referred to herein as "TTLE") are important components of the digestion of proteins by insects. In the mosquito, *Aedes aegypti*, an early trypsin that is found in the midgut of newly emerged females is replaced, following the blood meal, by a late trypsin. A female mosquito typically weighs about 2 mg and produces 4 to 6 µg of trypsin within several hours after a ingesting blood meal. Continuous boisynthesis at this rate would exhaust the available metabolic energy of a female mosquito; as a result, the mosquito would be unable to produce mature eggs, or even to find an oviposition site. To conserve metabolic energy, the mosquito regulates TTLE biosynthesis with a peptide hormone named Trypsin Modulating Oostatic Factor (TMOF). Mosquitoes produce TMOF in the follicular epithelium of the ovary 12–35 hours after a blood meal; TMOF is then released into the hemolymph where it binds to a specific receptor on the midgut epithelial cells, signaling the termination of TTLE biosynthesis.

This regulatory mechanism is not unique for mosquitoes; flesh flies, fleas, sand flies, house flies, dog flies and other pests which ingest protein as part of their diet have similar regulatory mechanisms.

In 1985, Borovsky purified an oostatic hormone 7,000-fold and disclosed that injection of a hormone preparation into the body cavity of blood imbibed mosquitoes caused inhibition of egg development and sterility (Borovsky, D. [1985] *Arch. Insect Biochem. Physiol.* 2:333–349). Following these observations, Borovsky (Borovsky, D. [1988] *Arch. Ins. Biochem. Physiol.* 7:187–210) reported that injection or passage of a peptide hormone preparation into mosquitoes inhibited the TTLE biosynthesis in the epithelial cells of the gut. This inhibition caused inefficient digestion of the blood meal and a reduction in the availability of essential amino acids translocated by the hemolymph, resulting in arrested egg development in the treated insect. Borovsky observed that this inhibition of egg development does not occur when the oostatic hormone peptides are inside the lumen of the gut or other parts of the digestive system (Borovsky, D. [1988], supra).

Following the 1985 report, the isolated hormone, (a ten amino acid peptide) and two TMOF analogues were disclosed in U.S. Pat. Nos. 5,011,909 and 5,130,253, and in a 1990 publication (Borovsky, et al. [1990] FASEBJ 4:3015–3020). Additionally, U.S. Pat. No. 5,358,934 discloses truncated forms of the full length TMOF which have prolines removed from the carboxy terminus, including the peptides YDPAP (SEQ ID NO. 14), YDPAPP (SEQ ID NO. 15), YDPAPPP (SEQ ID NO. 16), and YDPAPPPP (SEQ ID NO. 17).

Neuropeptides Y (NPY) are an abundant family of peptides that are widely distributed in the central nervous system of vertebrates. NPY peptides have also recently been isolated and identified in a cestode, a turbellarian, and in terrestrial and marine molluscs (Maule et al., 1991 "Neuropeptide F: A Novel Parasitic Flatworm Regulatory Peptide from *Moniezia expansa* (Cestoda: Cyclophylidea)" Parasitology 102:309–316; Curry et al., 1992 "Neuropeptide F: Primary Structure from the Turbellarian, *Arthioposthia triangulata*" Comp. Biochem. Physiol. 101C:269–274; Leung et al., 1992 "The Primary Structure of Neuropeptide F (NPF) from the Garden Snail, Helix aspersa" Regul. Pep. 41:71–81; Rajpara et al., 1992 "Identification and Molecular Cloning of Neuropeptide Y Homolog that Produces Prolonged Inhibition in Aplysia Neurons" Neuron. 9:505–513).

Invertebrate NPYs are highly homologous to vertebrate NPYs. The major difference between vertebrate and invertebrate NPYs occurs at the C-terminus where the vertebrate NPY has an amidated tyrosine (Y) whereas invertebrates have an amidated phenylalanine (F). Because of this difference, the invertebrate peptides are referred to as NPF peptides.

Cytoimmunochemical analyses of NPY peptides suggest that they are concentrated in the brain of various insects, including the Colorado potato beetle *Leptinotarsa decemlineata* (Verhaert et al., 1985 "Distinct Localization of FMRFamide- and Bovine Pancreatic Polypeptide-Like Material in the Brain, Retrocerebal Complex and Subesophageal Ganglion of the Cockroach *Periplaneta americana*" L. Brain Res. 348:331–338; Veenstra et al., 1985 "Immunocytochemical Localization of Peptidergic Neurons and Neurosecretory Cells in the Neuro-Endocrine System of the Colorado Potato Beetle with Antisera to Vertebrate Regulatory Peptides" Histochemistry 82:9–18). Partial purification of NPY peptides in insects suggests that both NPY and NPF are synthesized in insects (Duve et al., 1981 "Isolation and Partial Characterization of Pancreatic Polypeptide-like Material in the Brain of the Blowfly *alliphora vomitoria*" Biochem. J. 197, 767–770).

Researchers have recently isolated two neuropeptides with NPF-like immunoreactivity from brain extracts of the Colorado potato beetle. The researchers purified the peptides using $C_{18}$ reversed phase high pressure liquid chromatography (HPLC), and determined their structure using mass spectrometry. The deduced structures of these peptides are: Ala-Arg-Gly-Pro-Gln-Leu-Arg-Leu-Arg-Phe-amide (SEQ ID NO. 1) and Ala-Pro-Ser-Leu-Arg-Leu-Arg-Phe-amide (SEQ ID NO. 2) designated NPF I and NPF II, respectively (Spittaels, Kurt et al. [1996] "Insect Neuropeptide F (NPF)-Related Peptides: Isolation from Colorado Potato Beetle (*Leptinotarsa decemlineata*) Brain," Insect Biochem. Molec. Biol. 26(4):375–382).

BRIEF SUMMARY OF THE INVENTION

The subject invention provides materials and methods useful for the control of pests. In a specific embodiment the methods of the subject invention can be used for treating mosquito larvae to control mosquito populations. Specifically exemplified are recombinant hosts transformed to comprise and/or produce biological control agents capable of increasing the mortality of pests, including mosquitoes and mosquito larvae.

One aspect of the subject invention pertains to a composition comprising a host edible by mosquito larvae, wherein the cells of the host comprise a biological control agent that increases the mortality of the mosquito larvae. In a specific embodiment, the biological control agent inhibits biosynthesis of digestive enzymes, such as TTLE, thereby inhibiting food digestion. This inhibition of food digestion ultimately results in starvation and death of the mosquito larvae.

In a preferred aspect of the subject invention, an appropriate host is transformed with a polynucleotide encoding a polypeptide which acts to inhibit TTLE biosynthesis. Appropriate hosts include, but are not limited to, prokaryotic and eukaryotic cells, edible by pests including mosquito larvae. The biological control agents useful according to the subject invention include, but are not limited to, TMOF or functional equivalents thereof, NPF or functional equivalents thereof, and other agents identifiable by, for example, assays employing a TMOF receptor.

In a specific embodiment of the subject invention, salt water Chlorella, such as *Chlorella desiccata* are stably transformed with a plasmid carrying DNA encoding TMOF.

One embodiment of the present invention concerns a pesticide composition comprising a peptide having the formula:

$$A^1A^2A^3A^4A^5Fl \text{ (Formula I) (SEQ ID NO. 8)}$$

wherein:

$A^1$ is selected from the group consisting of A, D, F, G, M, P, S and Y;

$A^2$ is selected from the group consisting of A, D, E, F, G, N, P, S and Y;

$A^3$ is selected from the group consisting of A, D, F, G, L, P, S and Y;

$A^4$ is optionally present when $A^3$ is present and is selected from the group consisting of A, F, G, L and Y;

$A^5$ is optionally present when $A^4$ is present and is selected from the group consisting of A, F, L and P;

Fl is a flanking region which is optionally present and is selected from the group consisting of: P, PP, PPP, PPPP (SEQ ID NO. 9), and PPPPP (SEQ ID NO. 10).

Preferably, the peptide does not comprise $YDPAP_6$ (SEQ ID NO. 11), $DYPAP_6$ (SEQ ID NO. 12), $PAP_6$ (SEQ ID NO. 13), YDPAP (SEQ ID NO. 14), $YDPAP_2$ (SEQ ID NO. 15), $YDPAP_3$ (SEQ ID NO. 16), $YDPAP_4$ (SEQ ID NO. 17), NPTNLH (SEQ ID NO. 18) or DF-OMe.

In a more specific aspect the peptide or protein comprises an amino acid sequence which consists essentially of the amino acid sequence of Formula 1. In a preferred aspect, the amino acid sequence is a TMOF or NPF fragment and lacks TMOF or NPF amino acids adjacent to the amino acid sequence of Formula I. Preferably the fragment has from 2–5 amino acids of TMOF. In still another aspect, the peptide consists of the amino acid sequence of Formula I.

In various embodiments, either $A^3A^4A^5$, $A^3A^4A^5Fl$, $A^4A^5,Fl, A^5$ or $A^5Fl$ are not present. Where $A^5$ is not present, Fl may be attached directly to $A^4$. Where $A^4A^5$ is not present, Fl may be attached directly to $A^3$. Finally, where $A^3A^4A^5$ is not present, Fl may be attached directly to $A^2$.

Preferred peptides are selected from the group consisting of: AAP (SEQ ID NO. 19), ADP (SEQ ID NO. 20), ADPAP (SEQ ID NO. 21), APA (SEQ ID NO. 22), DAA (SEQ ID NO. 23), DF (SEQ ID NO. 24), DPA (SEQ ID NO. 25), DY (SEQ ID NO. 26), DYP (SEQ ID NO. 27), FAP (SEQ ID NO. 28), FDP (SEQ ID NO. 29), FDPAP (SEQ ID NO. 30), FSP (SEQ ID NO. 31), MPDYP5 (SEQ ID NO. 32), PAA (SEQ ID NO. 33), PAP (SEQ ID NO. 34), Y(D)DP (SEQ ID NO. 35), Y(D)DPAP (SEQ ID NO. 36), YAP (SEQ ID NO. 37), YD (SEQ ID NO. 38), YDA (SEQ ID NO. 39), YDAAP (SEQ ID NO. 40), YDF (SEQ ID NO. 41), YDFAP (SEQ ID NO. 42), YDG (SEQ ID NO. 43), YDLAP (SEQ ID NO. 44), YDP (SEQ ID NO. 45), (D)YDP (SEQ ID NO. 46), YDPAF (SEQ ID NO. 47), YDPAL (SEQ ID NO. 48), (D)YDPAP (SEQ ID NO. 49), YDPFP (SEQ ID NO. 50), YDPGP (SEQ ID NO. 51), YDPLP (SEQ ID NO. 52), YEPAP (SEQ ID NO. 53), YFPAP (SEQ ID NO. 54), YNPAP (SEQ ID NO. 55) and YSF (SEQ ID NO. 56).

A further embodiment of the present invention comprises a peptide having the formula $A^1A^2$ (Formula II) (SEQ ID NO. 62)

wherein $A^1$ is an amino acid selected from the group consisting of A, D, F, M, and Y, and $A^2$ is an amino acid selected from the group consisting of A, D, E, P, and Y.

In a preferred embodiment, the subject invention is directed to peptides of Formula II wherein $A^1$ and $A^2$ are independently selected from the group consisting of A, D, and Y.

Specifically exemplified as another embodiment are methods using an NPF peptide having the sequence Ala-Arg-Gly-Pro-Gln-Leu-Arg-Leu-Arg-Phe-amide (SEQ ID NO. 1) or Ala-Pro-Ser-Leu-Arg-Leu-Arg-Phe-amide (SEQ ID NO. 2).

The term "pesticidal polypeptide" is used herein to indicate NPF and TMOF peptides, as well as fragments, derivatives and analogues and functional equivalents of NPF and TMOF. The present invention also provides analogues of the pesticidal polypeptides which have one or more amino acid substitutions forming a branched peptide (e.g., by substitution with an amino acid or amino acid analogue having a free amino- or carboxy-side chain that forms a peptide bond with a sequence of one or more amino acids, including but not limited to prolines) or allowing circularization of the peptide (e.g., substitution with a cysteine, or insertion of a cysteine at the amino- or carboxy-terminus or internally, to provide a sulfhydryl group for disulfide bond formation).

The pesticidal polypeptides of the present invention are particularly advantageous because their smaller size permits more rapid and efficient penetration into the midgut. In addition, they are less expensive to produce by conventional chemical methods.

In one embodiment, the subject invention provides pesticidal polypeptides having a C-terminus arginine. In a preferred embodiment, these short polypeptides can be joined to form polymers of repeating units. Specifically exemplified herein is the $(DPAR)_4$ (SEQ ID NO. 61) polymer which can be broken into four DPAR (SEQ ID NO. 60) units in the gut of the pest. Advantageously, the short pesticidal polypeptides connected by arginine (or other readily cleavable residue) can penetrate the midgut of the pest efficiently.

Also included in this invention are addition salts, complexes, or prodrugs such as esters of the pesticidal polypeptide, especially the nontoxic pharmaceutically or agriculturally acceptable acid addition salts. The acid addition salts can be prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. Also, the N-terminus and C-terminus of the pesticidal polypeptides can be chemically modified to further inhibit proteolysis by metabolic enzymes.

The analogues of the pesticidal polypeptides of the present invention also include polypeptides having NPF and/or TMOF amino acid sequences in which one or more of the amino acid residues has been substituted by an amino acid in the D- conformation. The presence of D-conformation amino acids can inhibit the ability of proteases to degrade the peptides of the subject invention. Polypeptides having the above sequences in which only conservative substitutions have been made are also provided by the present invention.

Also, derivation of the pesticidal polypeptides with long chain hydrocarbons will facilitate passage through the cuticle into the pest body cavity. Accordingly, a further embodiment of the subject invention pertains to compositions comprising the pesticidal polypeptides bound to lipids or other carriers.

Yet another aspect of the subject invention pertains to polynucleotides encoding the pesticidal polypeptides of the subject invention. These polynucleotides can readily be synthesized by a person skilled in the art. The sequences may be used to transform an appropriate host to confer upon that host the ability to express the novel peptides. Hosts of particular interest include bacteria, algae, yeasts, and plants. Viruses may also be modified to comprise polynucleotide sequences encoding the pesticidal polypeptides of the present invention. For each of these hosts, the polynucleotides may be specifically designed by a person skilled in the art to utilize codons known to be optimally expressed in the particular hosts. Advantageous promoters are also readily incorporated into the polynucleotides. Bacteria, yeasts, plants, algae, viruses, and other hosts each may be used to produce peptides for further use, or these hosts can be used as vehicles for direct application of the peptide to the target pest. Plants can be transformed to make the plant toxic to a target pest species which feeds on that plant. Methods for transforming plant cells utilizing, for example, Agrobacteria are well known to those skilled in the art.

As used herein, the term "pesticidally effective" is used to indicate an amount or concentration of a pesticide which is sufficient to reduce the number of pests in a geographical area, as compared to a corresponding geographical area in the absence of the amount or concentration of the pesticide.

The term "pesticidal" is not intended to refer only to the ability to kill pests, but also includes the ability to interfere with a pest's life cycle in any way that results in an overall reduction in the pest population. For example, the term "pesticidal" included inhibition or elimination of reproductive ability of a pest, as well as inhibition of a pest from progressing from one form to a more mature form, e.g., transition between various larval instars or transition from larvae to pupa or pupa to adult. Further, the term "pesticidal" is intended to include all phases of a pest life cycle; thus, for example, the term includes larvicidal, ovicidal, and adulticidal action.

The word "transform" is broadly used herein to refer to introduction of an exogenous polynucleotide sequence into a prokaryotic or eukaryotic cell by any means known in the art (including, for example, direct transmission of a polynucleotide sequence from a cell or virus particle as well as transmission by infective virus particles and transmission by any other known means for introducing a polynucleotide into a cell), resulting in a permanent or temporary alteration of genotype and in an immortal or non-immortal cell line.

The terms "peptide," "polypeptide," and "protein" as used herein are intended to refer to amino acid sequences of any length.

Another aspect of the subject invention pertains to a method of controlling pests comprising administering to said pest an effective amount of a peptide of the subject invention.

The subject invention provides pesticidal compositions wherein the pesticidal polypeptides are formulated for application to the target pests, or their situs. In a specific embodiment, the present invention provides recombinant hosts which express a polynucleotide encoding a pesticidal polypeptide to produce the pesticidal polypeptide. The recombinant host may be, for example, prokaryotic or eukaryotic. In a specific example, yeast or algae are transformed to express a pesticidal polypeptide of the subject invention. The transformed hosts are then applied to water areas where mosquito larvae will ingest the transformed host resulting in control of the mosquitoes by the pest control agent.

Preferably, the subject peptides have an $LD_{50}$ against mosquito larvae of less than 3.0 μmoles/ml. More preferably, the peptides have an $LD_{50}$ of less than 2.0 μmoles/ml, and, most preferably, the peptides have an $LD_{50}$ of less than 1.0 μmoles/ml. As used herein, "$LD_{50}$" refers to a lethal dose of a peptide able to cause 50% mortality of larvae maintained on ad iet of 1 mg/ml autoclaved yeast (Borovsky and Mahmood [1995] "Feeding the mosquito *Aedes aegypti* with TMOF and its analogs; effect on trypsin biosynthesis and egg development," *Regulatory Peptides* 57:273–281).

Another aspect of the subject invention pertains to methods of controlling pests comprising preparing a host to produce a pesticidal polypeptide wherein the host is edible by the target pest and administering the host to the target pest.

Another aspect of the subject invention pertains to pesticidal polypeptides and other pesticidal compounds used in conjunction with a marker to aid in the administration and/or monitoring of the biological control agent. Such markers include, for example, Green Fluorescent Protein (GFP). This protein fluoresces and provides a means to determine whether target pests, such as mosquitoes, are eating or have been treated by the biological control agent. Target pests which have eaten the biological control agent fused with the GFP will fluoresce. This fluorescence can be employed as an analytical measurement which indicates whether target pests such as mosquito larvae are indeed consuming the pesticidal polypeptide or other pesticidal compound Such measurements are useful for determining the amount of pesticidal polypeptide which must be applied to maintain a pesticidally effective amount of the pesticidal polypeptide.

BRIEF DESCRIPTION OF THE DRAWINGS

FIGS. 2A and 2B depict the introduction of the pYDB2 plasmid into yeast.

BRIEF DESCRIPTION OF THE SEQUENCES

Figure 1:
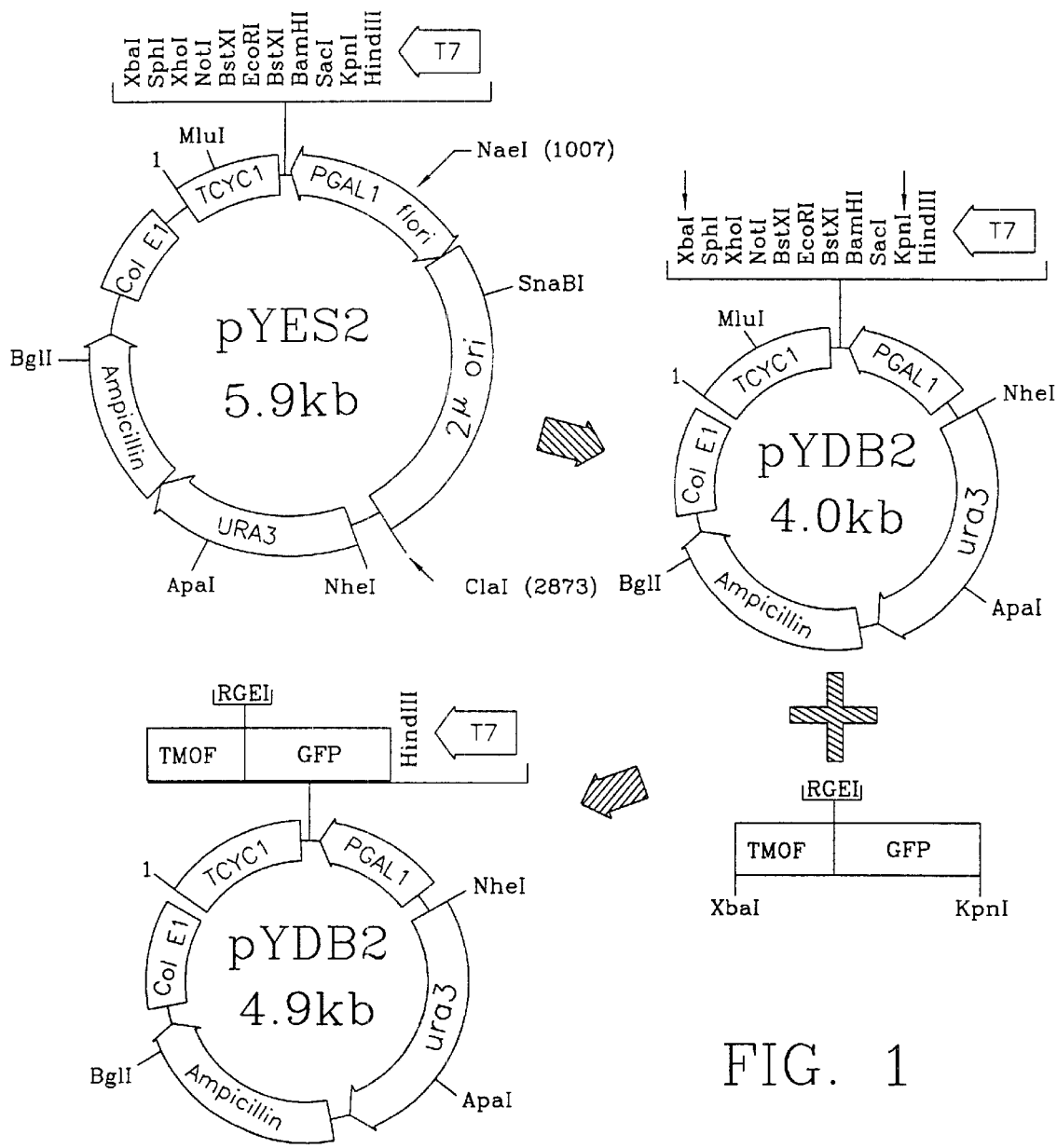
FIG. 1 is a schematic of the construction of the pYDB2 plasmid.

SEQ ID NO. 1 is a neuropeptide designated NPF I.

SEQ ID NO. 2 is a neuropeptide designated NPF II.

SEQ ID NO. 3 is a polynucleotide encoding an amino acid sequence of a TMOF receptor.

SEQ ID NO. 4 is an amino acid sequence of a TMOF receptor.

SEQ ID NO. 5 is a forward primer useful according to the subject invention.

SEQ ID NO. 6 is a backward primer useful according to the subject invention.

SEQ ID NO. 7 is an oligonucleotide useful according to the subject invention.

SEQ ID NO. 8–59 are TMOF peptides useful according to the subject invention.

SEQ ID NO. 60–61 are TMOF-R analogue peptides useful according to the subject invention.

SEQ ID NO. 62 is a TMOF peptide useful according to the subject invention.

SEQ ID NO. 63 is an unamidated version of the neuropeptide designated NPF I (SEQ ID NO. 1).

SEQ ID NO. 64 is an unamidated version of the neuropeptide designated NPF II (SEQ ID NO. 2).

SEQ ID NO. 65 is the TMOF synthetic gene sense strand useful according to the subject invention.

SEQ ID NO. 66 is the TMOF synthetic gene antisense strand useful according to the subject invention.

SEQ ID NO. 67–71 are TMOF-R analogue peptides useful according to the subject invention.

DETAILED DISCLOSURE OF THE INVENTION

The subject invention is directed to materials and methods for controlling pest populations. Specifically exemplified herein are compositions comprising hosts which contain, are associated with, and/or which express pesticidal polypeptides and other biological control agents. Also exemplified herein are methods of controlling pests, such as mosquitoes, employing hosts which contain, are associated with, and/or which express the pesticidal polypeptides or other pesticidal compounds. Preferably, the pesticidal agents have the ability to inhibit biosynthesis of TTLE. The term "pest" as used herein includes mosquitoes, insects and other organisms which adversely affect humans, plants or animals. This includes pests that remove blood, tissue or any other fluid from their prey or host. Pests controlled according to the subject invention include those which have a mechanism for regulating digestive enzymes, such as TTLE, which mechanism involves the binding of a ligand to a receptor to increase or decrease such enzymes, e.g., TMOF or NPF binding to its receptor. Examples of pests which can be controlled according to the subject invention include, but are not limited to, mosquitoes, fleshflies, fleas, sandflies, houseflies, dogflies, and insects which attack plants.

In a preferred embodiment, the present invention provides a host cell or virus particle which contains, is associated with and/or produces a pesticidal polypeptide (a "pesticidal cell"). The host can be a prokaryotic or eukaryotic cell which is transformed to express a pesticidal polypeptide or other biological control agent. The host may also be a viral particle which has been prepared to deliver a polynucleotide encoding a pesticidal polypeptide to a cell. The host can be prepared by transforming the host with a polynucleotide encoding a peptide capable of inhibiting biosynthesis of digestive enzymes, such as TTLE. In specific embodiments, the host cell is Chlorella or yeast and the peptide is TMOF, NPF, a TMOF receptor-binding compound, or a functional analogue, derivative, fragment or other functional equivalent of the TMOF, NPF or other TMOF receptor-binding compound.

The pest control compositions according to the subject invention include compounds which comprise an NPF or TMOF peptide or a TMOF receptor-binding compound, or analogue, derivative, fragment or other functional equivalent of the TMOF, NPF or other TMOF receptor-binding compound (collectively referred to herein as "pesticidal polypeptides"). One or more pesticidal polypeptides may be provided as a component of a formulation, or as the sole component of the pesticidal composition. The pesticidal compositions may further comprise a carrier solution, compound, or molecule. Pesticidal compositions of the subject invention may also comprise pesticidal polypeptides contained in or associated with a prokaryotic or eukaryotic cell, such as a plant, animal or fungi cell, and may also be contained in or associated with a viral particle. Examples include, but are not limited to, transformed bacteria, animal cells, algae, fungi, yeast, viruses, and plants that comprise a polynucleotide encoding a pesticidal polypeptide.

The term "functional equivalent" as used herein refers to a full-length NPF or TMOF peptide, or an analogue, derivative, fragment or extension thereof which retains some or all of the biological activity of the corresponding NPF or TMOF peptide. Functional equivalents also include, for example, an NPF or TMOF peptide in a salt, complex, analogue, or derivative form. The term "NPF polypeptide" refers to compounds which comprise an NPF peptide and includes analogues, fragments, derivatives and other functional equivalents thereof. The term "TMOF polypeptide" refers to compounds which comprise a TMOF peptide and includes analogues, fragments, derivatives and other functional equivalents thereof.

The pesticidal polypeptides of the subject invention may be presented as fusion proteins or peptides, the amino acid sequence of which includes one or more polypeptides of the present invention and may optionally include one or more heterologous polypeptides. In various specific embodiments, two or more of the polypeptides are linked, for example, by peptide bonds between the N-terminus of one portion and the C-terminus of another portion. In other aspects, one or more of the polypeptides can be linked to one or more heterologous peptides or proteins to form pesticidal fusion peptides. Molecules comprising such portions linked by hydrocarbon linkages are also provided. Derivatives of the foregoing fusion proteins are also provided (e.g., branched, cyclized, N- or C-terminal chemically modified, etc.).

Pesticidal polypeptides in which only conservative substitutions have been made are also provided by the present invention. The present invention also provides analogues which have one or more amino acid substitutions forming a branched peptide (e.g., by substitution with an amino acid or amino acid analogue having a free amino- or carboxy-side chain that forms a peptide bond with a sequence of one or more amino acids including, but not limited to, prolines) or allowing circularization of the peptide (e.g., by substitution with a cysteine or insertion of a cysteine at the amino- or carboxy-terminus or internally to provide a sulfhydryl group for disulfide bond formation), are also provided.

Nonclassical amino acids or chemical amino acid analogues can be introduced as a substitution, insertion or addition into the pesticidal polypeptides of the present invention. Non-classical amino acids include but are not limited to the D-isomers of the common amino acids, 2,4-diaminobutyric acid, a-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Furthermore, the amino acid can be D (dextrorotary) or L (levorotary). Dextrorotary amino acids are indicated herein by a parenthetical D, i.e., "(D)", immediately preceding the dextrorotary amino acid.

Thus, the pesticidal polypeptides, analogues, fragments, derivatives, and other functional equivalents thereof, include peptides containing, as a primary amino acid sequence, all or part of an exemplified polypeptide sequence including altered sequences in which functionally equivalent amino acid residues are substituted for residues within the sequence resulting in a peptide which is functionally active. For example, one or more amino acid residues within the sequence can be substituted by another amino acid of a similar polarity which acts as a functional equivalent, resulting in a silent alteration. Conservative substitutions for an amino acid within the sequence may be selected from other members of the class to which the amino acid belongs (see Table 1). The pesticidal polypeptides, and fragments, derivatives and analogues thereof can be made by chemical peptide synthesis or by recombinant production from a polynucleotide encoding the pesticidal polypeptides.

In a specific embodiment, the subject invention is directed toward a method of controlling blood-ingesting pests comprising preparing a treatment comprising NPF and/or TMOF compounds and applying said treatment to said blood-ingesting pests. In another embodiment these peptides are used to control agricultural pests.

The transformed pesticidal polypeptide-producing host can be administered by bringing the host into contact with the habitat of a target pest. For example, where the target pest is a mosquito, the pesticidal polypeptide can be applied to water in environments known to be natural habitats for mosquitoes and mosquito larvae. In one embodiment, the host is alive and will proliferate in the environment. Alternatively, the host may be applied in a non- living state. Preferably, the host is palatable to the target pest leading to the ingestion of the transformed host. Once in the gut of the target, the host may further divide and grow, but many host cells will lyse. This lysis releases the biological control agent in the gut of the target pest, ultimately resulting in the death of the pest.

Mosquitoes are preferred target pests according to the present invention. Mosquito larvae grow in wet environments, such as marshes or ponds, and they consume cells, typically found in such environments. Algae typically comprise a significant portion of a mosquito larvae's diet, and as a result, algae are preferred organisms which can be transformed according to the subject invention to express agents known to inhibit biosynthesis of TTLE. Thus, in one embodiment, the present invention is directed to a composition comprising an algae cell transformed to express a pesticidal polypeptide. The algae cell is preferably a unicellular algae and is most preferably a unicellular green algae. With the benefit of the teachings provided herein, algae, such as Chlorella, can be transformed to express pesticidal polypeptides. In a specific embodiment, the microbe that is transformed is a salt water Chlorella such as *Chlorella desiccata.*

Preferably, the algae is transformed with a polynucleotide encoding a pesticidal polypeptide having the ability to inhibit biosynthesis of one or more pest digestive enzymes such as TTLE. As used herein, reference to "functional equivalents" includes, without limitation, truncated or extended TMOF or NPF polypeptides (as compared to native NPF or TMOF polypeptides) as well as analogues and derivatives of NPF and TMOF polypeptides, where such truncated peptides, extended peptides, analogues and derivatives exhibit partial, equal or improved functional characteristics as compared to the native NPF and TMOF polypeptides. Additionally, the pesticidal polypeptides of the present invention include non-TMOF and non-NPF polypeptides and other compounds which bind to a TMOF or NPF receptor. Thus, the peptide can be a protein or other molecule as identified through, for example, assays employing a TMOF receptor described herein.

Further, to aid in the administration and quantification of delivery of the transformed host, various markers can be used to test whether the transformed host exists in vitro or in the environment and/or whether pests, such as mosquito larvae, have ingested the pesticidal host. One example of such a marker is the Green Fluorescent Protein (GFP). Using known techniques, a fusion protein containing both the GFP and a biological control agent of the subject invention can be prepared. Upon ingestion of a host containing this fusion protein, the mosquito larvae will fluoresce. This fluorescence facilitates quantification of the amount of host administered and the amount of host being eaten by the mosquito larvae, which, permits adjustment of the application rate of the transformed hosts to ensure the continued presence of a pesticidally effective concentration of the host in the environment of the target pest. The amount of host administered can thereby be precisely refined, improving the efficiency of product use and reducing overall costs of treatment.

In an alternative embodiment, the host can be a synthetic capsule containing a biological control agent. The capsule can comprise, for example, a microcontainer such as a microsphere having an outer shell which can degrade when exposed to the conditions of the larvae gut. Materials suitable for selective degrading under such conditions are numerous and commonly known in the art. These microcontainers can be deposited in larvae habitats whereby they will be passively ingested during the course of normal feeding.

In addition, there are numerous agents known to infect insects such as mosquitoes. These agents can, for example, comprise certain types of bacteria and viruses, such as baculoviruses and entomopoxviruses. Upon infection of a pest organism, the production of biological control agents by the pest's own cells will result in the death of the pest.

Various biological control agents can be used in the compositions of the subject invention. For example, U.S. Pat. Nos. 5,011,909; 5,130,253; and 5,358,934 describe polynucleotides encoding TMOF and functional equivalents thereof.

In one embodiment, the subject invention pertains to the pesticidal use of peptides which comprise the amino acid sequence of Formula I (SEQ ID NO. 8). In a preferred embodiment, the subject invention is directed to peptides which comprise the amino acids A, D, and Y. Preferably, the subject peptides have an $LD_{50}$ against mosquito larvae of less than 3.0 $\mu$moles/ml. More preferably, the peptides have an $LD_{50}$ of less than 2.0 $\mu$moles/ml, and, most preferably, the peptides have an $LD_{50}$ of less than 1.0 $\mu$moles/ml. As used herein, "$LD_{50}$" refers to a lethal dose of a peptide able to cause 50% mortality of larvae maintained on a diet of 1 mg/ml autoclaved yeast (Borovsky and Mahmood [1995] supra).

In one embodiment, the pesticidal polypeptide comprises a repeating unit of at least 3 amino acids. There may be, for example, from 2 to 10 or more repeating units. Preferably, the repeating unit is connected through at least one amino acid which is cleaved by a pest gut enzyme. As used herein, a pest gut enzyme is an enzyme which is present in the gut of a pest. Preferably, the pest is a mosquito or a lepidopteran. In a specific embodiment the repeating units are connected through an arginine.

TMOF analogues (5 to 8 amino acids in length, and polymers of these analogues) in which Arg was added at the C-terminus were evaluated to determine their effect on larval growth and development. A series of analogues were synthesized and tested by feeding them to mosquito larvae at concentrations of (0.5 to 5.0 mg/ml; Table 4). Concentrations of 2.0 to 0.065 mg/ml were used to feed mosquito larvae and calculate the Lethal Dose at 50% mortality ($LD_{50}$; Table 4) of the TMOF analogues. Several analogues that were effective at $LC_{50}$ of 0.24 to 0.048 mM were chosen and were injected into $2^{nd}$ instar *Heliothis virescens* and the inhibition of trypsin biosynthesis was followed for 24 hours (Table 5). In both cases larval death and trypsin biosynthesis inhibition was noted (Table 4 and 5). These results indicate that short TMOF analogues or polymers of these analogues with Arg at the termini can be used efficiently to block larval growth by shutting down the enzyme that digests the food in both mosquitoes and Heliothis. The advantage of using short analogues connected by Arg is that they can be digested in the gut into short TMOF analogues that can penetrate the midgut much faster than longer analogues.

The skilled artisan, having the benefit of the instant description, can use techniques well-known in the art to transform a host to express the pesticidal polypeptides of the present invention. The transformed host then expresses the polynucleotides.

In a specific embodiment exemplified herein, yeast cells that were transformed to express GFP-TMOF were fed to mosquito larvae and compared with controls in which the GFP-TMOF gene was not part of the yeast genome. Larvae fed on either (1) live recombinant yeast cells, or (2) heat inactivated cells, starved and died within 5 to 6 days. In contrast, controls fed on normal yeast cells grew and developed normally, producing adult mosquitoes.

These results show that recombinant yeast can be utilized as a vehicle to control mosquito populations. Using yeast cells that synthesize GFP has the advantage that the amount of pesticidal polypeptide consumed by mosquito larvae can be determined by measuring the fluorescence of the mosquito larvae. This information permits users to ensure that the pesticidal compositions are applied at a sufficient rate to adequately control the mosquito population.

TMOF Receptors and Polynucleotides

In one embodiment, the subject invention is directed to the control of pests using a pesticidal polypeptide or other compound which binds to or otherwise associates with a TMOF receptor. Specifically exemplified herein is a TMOF receptor comprising the amino acid sequence shown in SEQ ID NO. 4. Preferably, the polypeptide is encoded by a complete nucleotide sequence of a TMOF receptor gene or fragments or mutants thereof which encode polypeptides having TMOF receptor activity. In a specific embodiment, the TMOF receptor is encoded by a polynucleotide sequence comprising the coding sequence (nucleotides I - 186) shown in SEQ ID NO. 3 or other polynucleotide sequence with codons encoding the amino acid sequence of SEQ ID NO. 4.

Isolated TMOF receptors can be used to produce antibodies according to known techniques. These antibodies may be monoclonal or polyclonal, and can be used to screen an expression library to identify other clones expressing polypeptides having TMOF receptor activity. Alternatively, these antibodies may be used to identify TMOF receptors from their natural material, such as mosquito or insect gut material.

A specific TMOF receptor sequence is exemplified herein. This sequence is merely exemplary of TMOF receptors. Variant or equivalent receptors (and nucleotide sequences coding for equivalent receptors) having the same or similar TMOF receptor activity can also be utilized. Equivalent receptors will typically have amino acid homology with the exemplified receptor. This amino acid identity will typically be greater than 60%, preferably be greater than 75%, more preferably greater than 80%, more preferably greater than 90%, and can be greater than 95%. These identities are determined using standard alignment techniques. The amino acid homology will be highest in critical regions of the receptor which account for biological activity or are involved in the determination of three- dimensional configuration which ultimately is responsible for the biological activity. In this regard, certain amino acid substitutions are acceptable and can be expected if these substitutions are in regions which are not critical to activity or are conservative amino acid substitutions which do not affect the three- dimensional configuration of the molecule. For example, amino acids may be placed in the following classes: non- polar, uncharged polar, basic, and acidic. Conservative substitutions whereby an amino acid of one class is replaced with another amino acid of the same type fall within the scope of the subject invention so long as the substitution does not completely eliminate the biological activity of the compound; however, preferred substitutions are those which result in the retention of most or all of the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not completely eliminate the biological activity of the receptor; however, preferred substitutions are those which result in the retention of most or all of the biological activity of the compound.

The use of polynucleotide probes is well known to those skilled in the art. In one specific example, a cDNA library for mosquito or insect gut cells can be created by routine means, and DNA of interest can be isolated from the cDNA library. Polynucleotides of the subject invention can be used to hybridize with DNA fragments of the constructed cDNA-library, allowing identification of and selection (or "probing out") of the genes of interest, i.e., those nucleotide sequences which hybridize with the probes of the subject invention and encode polypeptides having TMOF receptor activity. The isolation of these genes can be performed by a person skilled in the art having the benefit of the instant disclosure, using techniques which are well-known in the molecular biology art.

Thus, it is possible, without the aid of biological analysis, to identify polynucleotide sequences encoding TMOF receptors. Such a probe analysis provides a rapid method for identifying genes encoding TMOF receptors from a wide variety of hosts. The isolated genes can be inserted into appropriate vehicles which can then be used to transform a suitable host.

Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under moderate to high stringency conditions by techniques well known in the art, as described, for example, in Keller, G. H., M. M. Manak [1987] DNA Probes, Stockton Press, New York, N.Y., pp. 169–170.

Examples of various stringency conditions are provided herein. Hybridization of immobilized DNA on Southern blots with $^{32}$P-labeled gene-specific probes can be performed by standard methods (Maniatis et al. [ 1982] *Molecular Cloning: A Laboratory Manual*, Cold Spring Harbor Laboratory, New York). In general, hybridization and subsequent washes can be carried out under moderate to high stringency conditions that allow for detection of target sequences with homology to the exemplified polynucleotide sequence. For double-stranded DNA gene probes, hybridization can be carried out overnight at 20–25±C below the melting temperature (Tm) of the DNA hybrid in 6×SSPE, 5×Denhardt's solution, 0.1% SDS, 0.1 mg/ml denatured DNA. The melting temperature is described by the following formula:

Tm=81.5° C.+16.6 Log[Na+]+0.41(%G+C)−0.61 (%formamide)−600/length of duplex in base pairs (Beltz et al. [1983] *Methods of Enzymology*, R. Wu, L. Grossman and K. Moldave [eds.] Academic Press, New York 100:266–285).

Washes are typically carried out as follows:

(1) twice at room temperature for 15 minutes in 1×SSPE, 0.1% SDS (low stringency wash);

(2) once at Tm-20° C. for 15 minutes in 0.2×SSPE, 0.1% SDS (moderate stringency wash).

For oligonucleotide probes, hybridization can be carried out overnight at 10–20° C. below the melting temperature (Tm) of the hybrid in 6×SSPE,5×Denhardt's solution, 0.1% SDS, 0.1 mg/ml denatured DNA. Tm for oligonucleotide probes can be determined by the following formula:

Tm (° C.)=2(number T/A base pairs)+4(number G/C base pairs) (Suggs, S.V., T. Miyake, E. H. Kawashime, M. J. Johnson, K. Itakura, and R. B. Wallace [1981] ICN-UCLA *Symp. Dev. Biol. Using Purified Genes*, D. D. Brown [ed.], Academic Press, New York, 23:683–693).

Washes can be carried out as follows:

(1) twice at room temperature for 15 minutes 1×SSPE, 0.1% SDS (low stringency wash);

(2) once at the hybridization temperature for 15 minutes in 1×SSPE, 0.1% SDS (moderate stringency wash).

In general, salt and/or temperature can be altered to change stringency. With a labeled DNA fragment>70 or so bases in length, the following conditions can be used:

Low: 1 or 2×SSPE, room temperature

Low: 1 or 2×SSPE, 42° C.

Moderate: 0.2× or 1×SSPE, 65° C.

High: 0.1×SSPE, 65° C.

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

Identification of Pesticidal Polypeptides and other Pesticidal Compounds. The TMOF receptors can advantageously be used to identify pesticidal polypeptides and other pesticidal compounds which activate the TMOF receptor. As noted above, activation of the TMOF receptor inhibits biosynthesis of TTLE, thereby inhibiting digestion of proteins and peptides and decreasing the availability of essential amino acids. A person skilled in the art, having the benefit of the instant disclosure, can utilize the TMOF receptors described herein to identify novel pesticidal polypeptides and other non-peptide pesticidal compounds. In one embodiment, the TMOF receptor can be purified from its natural sources using, for example, antibodies to the TMOF receptor to obtain the purified protein. This purified protein can then be used to identify compounds which bind to the receptor. Compounds thus identified can then be further evaluated using, for example, appropriate bioassays to confirm and/or characterize the pest control activity of the compound.

As an alternative to purifying TMOF receptors from their natural material, recombinant TMOF receptor protein can be expressed in an appropriate recombinant host which has been transformed with a polynucleotide sequence encoding the TMOF receptor. The polynucleotide sequence used to transform the appropriate host may comprise, for example, the polynucleotide coding sequence disclosed in SEQ ID NO. 3. The host may be transformed so as to express the TMOF receptor at the cell surface or, alternatively, the TMOF receptor may be retained intracellularly or secreted into the surrounding media. In any case, the expressed TMOF receptor may be isolated from the recombinant host using techniques known to those skilled in the art. The recombinant purified protein can then be used as described above to identify compounds which bind to the receptor. As an alternative embodiment, the receptor expressed at the surface of the recombinant cell can be used in conjunction with the whole cell to identify compounds which bind to the receptor.

In another embodiment, TMOF receptors of the subject invention can be applied to a chip or other suitable substrate to facilitate high throughput screening of potential pesticidal polypeptides and other non-peptide pesticidal compounds.

Once compounds are identified which bind to the TMOF receptor, their pesticidal activity can be confirmed and/or characterized using bioassays known to those skilled in the art. The pesticidal polypeptides and other pesticidal compounds of the subject invention can have activity against a variety of pests, for example, agricultural pests which attack plants as well as pests of animals which attack humans, agricultural animals, and/or domestic animals.

Production of recombinant hosts. The various methods employed in the preparation of the plasmids and transformation of host organisms are well known in the art; some of these methods are described in U.S. Pat. Nos. 5,011,909 and 5,130,253. These patents are incorporated herein by reference. Plasmid preparation procedures are also described in Maniatis et al. (1982) *Molecular Cloning: A Laboratory Manual*, Cold Spring Harbor Laboratory, New York. From these references and many others it can be seen that it is within the skill of those in the genetic engineering art to extract DNA from microbial cells, perform restrictions enzyme digestions, electrophorese DNA fragments, tail and anneal plasmid and insert DNA, ligate DNA, transform cells, e.g., *E. coli* or plant cells, prepare plasmid DNA, electrophorese proteins, and sequence DNA.

Various markers may be employed for the selection of transformants, including biocide resistance, particularly to antibiotics such as ampicillin, tetracycline, trimethoprim, chloramphenicol and penicillin; toxins, such as colicin; and heavy metals, such as mercuric salts. Alternatively, complementation (providing an essential nutrient to an auxotrophic host) may be employed.

The polynucleotide sequences of the subject invention can be introduced directly into the genome of the transformable host cell or can first be incorporated into a vector which is then introduced into the host. Exemplary methods of incorporation include transduction by recombinant phage or cosmids, transfection where specially treated host bacterial cells can be caused to take up naked phage chromosomes, and transformation by calcium precipitation. These methods are well known in the art. Exemplary vectors include plasmids, cosmids and phages.

It is well known in the art that when synthesizing a gene for improved expression in a host cell it is desirable to design the gene such that its frequency of codon usage approaches the frequency of preferred codon usage of the host cell. For purposes of the subject invention, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable to limit this analysis to genes that are highly expressed by the host cell.

Thus, in one embodiment of the subject invention, cells can be genetically engineered, e.g., transformed with polynucleotides encoding the subject peptides to attain desired expression levels of the subject peptides. To provide genes having enhanced expression, the DNA sequence of the gene can be modified to comprise codons preferred by highly expressed genes to attain an A+T content in nucleotide base composition which is substantially that found in the transformed host cell. It is also preferable to form an initiation sequence optimal for the host cell and to eliminate sequences that cause destabilization, inappropriate polyadenylation, degradation and termination of RNA, and to avoid sequences that constitute secondary structure hairpins and RNA splice sites. For example, in synthetic genes, the codons used to specify a given amino acid can be selected with regard to the distribution frequency of codon usage employed in highly expressed genes in the host cell to specify that amino acid. As is appreciated by those skilled in the art, the distribution frequency of codon usage utilized in the synthetic gene is a determinant of the level of expression.

Assembly of the polynucleotide sequences of this invention can be performed using standard technology known in the art. For example, a structural gene designed for enhanced expression in a host cell can be assembled within a DNA vector from chemically synthesized oligonucleotide duplex segments. Preferably, the DNA vector or construct has an operable promoter and suitable termination signals. The polynucleotide sequence can then be introduced into a host cell and expressed by means known in the art. Preferably, the pesticidal polypeptide or receptor produced upon expression of the nucleotide sequence is functionally equivalent to the purified peptide. According to the subject invention, "functionally equivalent" refers to retention of function such as, for example, pest control activity.

Furthermore, chimeric polypeptides may be made and used according to the subject invention. These chimeric polypeptides may comprise two or more pesticidal polypeptides of the present invention linked by peptide bonds, disulfide bonds or other chemical bonds known in the art for joining amino acids, and may optionally include one or more heterologous polypeptides joined in like manner to one or more pesticidal polypeptides of the present invention. The portions that are combined need not be pesticidal, so long as the combination of portions creates a chimeric protein which is pesticidal. The chimeric polypeptides may include portions from toxins which do not necessarily act upon the TMOF receptor. For example, toxins from *Bacillus thuringiensis* (B.t.) and their various toxin domains are well known to those skilled in the art; e.g., *B.t. israeliensis, B.t. tenebrionis, B.t. san diego, B.t. aizawai, B.t. subtoxicus, B.t. alesti, B.t. gallaeriae, B.t. sotto, B.t. kurstaki, B.t. berliner, B.t. tolworthi, B.t. dendrolimus* and *B.t. thuringiensis*, as well as B.t. toxins described in U.S. Pat. No. 5,686,069, including various delta-endotoxins.

With the teachings provided herein, one skilled in the art can readily make and use the various polypeptides and polynucleotide sequences described herein.

The polynucleotide sequences and pesticidal polypeptides useful according to the subject invention include not only the exemplified sequences but also fragments of these sequences, variants, mutants, and fusion proteins which retain the characteristic pesticidal activity of the peptides specifically exemplified herein. As used herein, the terms "variants" or "variations" of genes refer to nucleotides having different nucleotide sequences encoding the same peptides or encoding equivalent peptides having pesticidal activity. As used herein, the term "equivalent peptides" refers to analogues, derivatives, fragments and other variants having the same or similar biological activity as the exemplified peptides which activity may be increased or reduced but which is not entirely eliminated.

Variations of genes may be readily constructed using standard techniques for making point mutations. Also, fragments of these genes can be made using commercially available exonucleases or endonucleases according to standard procedures. For example, enzymes such as BAL31 or site-directed mutagenesis can be used to systematically excise nucleotides from the ends of these gene fragments. Also, genes encoding active fragments may be obtained using a variety of restriction enzymes. Proteases may be used to directly obtain active fragments of these peptides.

Polynucleotide sequences encoding pesticidal polypeptides of the subject invention can be introduced into a wide variety of microbial or plant hosts, such that expression of the gene results, directly or indirectly, in the production and maintenance of the pesticide. With suitable microbial hosts, e.g. yeast or Chlorella, the microbes can be applied to the situs of the pest where they will proliferate and be ingested, resulting in control of the pest. Alternatively, the microbe hosting the gene can be killed and treated under conditions that retain and/or prolong the activity of the pesticidal polypeptide and stabilize the cell. The treated cell, which retains the toxic activity, can then be applied to the environment of the target pest. In one embodiment, the host is transformed such that the gene encoding the pesticidal polypeptide is only expressed or maintained for a relatively short period of time, such as days or weeks, so that the material does not persist in the environment.

A wide variety of means are available for introducing a polynucleotide sequence encoding a pesticidal polypeptide into a microorganism host under conditions which allow for stable maintenance and expression of the gene. These methods are well known to those skilled in the art and are described, for example, in U.S. Pat. No. 5,135,867, which is incorporated herein by reference.

Synthetic genes encoding peptides that are functionally equivalent to the pesticidal polypeptides of the subject invention can also be used to transform hosts. Methods for the production of synthetic genes can be found for example, in U.S. Pat. No. 5,380,831.

Recombinant cells expressing a pesticidal polypeptide can be treated to prolong the pesticidal activity of the polypeptide and optionally to stabilize the cell. Pesticide microcapsules can be formed which comprise the pesticidal polypeptide within a stabilized cellular structure and protect the pesticidal polypeptide when the microcapsule is applied to the environment of the target pest. Suitable host cells include prokaryotes and eukaryotes. Preferred hosts include prokaryotes and lower eukaryotes, such as algae and fungi.

The cell is preferably intact and substantially in the proliferative form when treated, rather than in a spore form.

Treatment of the microbial cell, e.g., a microbe comprising the polynucleotide sequence encoding the pesticidalpolypeptide, can be by chemical or physical means, or by a combination of chemical and/or physical means, so long as the technique does not completely eliminate the pesticidal properties of the pesticidal polypeptides and does not diminish the cellular capability of protecting the pesticidal polypeptide. Methods for treatment of microbial cells are disclosed in U.S. Pat. Nos. 4,695,455 and 4,695,462, which are incorporated herein by reference.

Formulations and Administration. As would be appreciated by a person skilled in the art, the pesticidal concentration will vary widely depending upon the nature of the particular formulation, particularly whether it is a concentrate or to be used directly. The pesticide will be present in at least about 0.0001% by weight and may be 100% by weight. The dry formulations will have from about 0.0001–95% by weight of the pesticide while the liquid formulations will generally be from about 0.0001–60% by weight of the solids in the liquid phase. The formulations that contain cells will generally have from about 1 to about $10^{10}$ cells/mg. These formulations will be administered at about 50 mg (liquid or dry) to 1 kg or more per hectare.

In applications to the environment of the target pest, the transformant strain can be applied to the natural habitat of the pest in a living or non-living state. When applied in a living state, the transformant strain may grow in the pest upon ingestion while producing the pesticidal polypeptide, which will have a deleterious effect on the pest. The organism may be applied by pouring, spraying, soaking, injection into the soil, seed coating, seedling coating or spraying, or the like.

In aquatic environments, pest control may be attained at or below the surface by adjusting the specific gravity of the microbe. Where the pesticidal polypeptide is applied as a component of a transformant microbe, depth control may be accomplished by varying the lipid content of the transformant microorganism strain. It is known that indigenous aquatic algae float due to their lipid content. A variation in lipid content will allow the transformant strain to be distributed at desired depths below the water surface.

Pesticidal polypeptides may also be formulated as tablets, pellets, briquettes, bricks or the like, which maintain the pesticidal polypeptide at a specific depth in an aqueous environment. In one embodiment, the compositions of the present invention are formulated to float on the surface of an aqueous medium; in another embodiment, they are formulated to maintain a depth of 0 to 2 feet in an aqueous medium; in yet another embodiment, the compositions are formulated to sink in an aqueous medium.

For commercial formulations, the organisms may be maintained in a nutrient medium (e.g., yeast extract or L-broth) which maintains selectivity and results in a low rate of proliferation. To prepare the organism for application, the non-proliferating concentrate may be introduced into an appropriate selective nutrient medium, grown to high concentration, generally from about 1 to $10^9$ cells/ml and may then be employed for introduction into the environment of the pest.

All of the U.S. patents and other references cited herein are hereby incorporated by reference, as are U.S. patent application Ser. No. 09/295,849, (UF-216) "Neuropeptides and their use for Pest Control"; U.S. patent application Ser. No. 09/296,113, (UF-224) "Materials and Methods Useful for the Control of Insect Larvae"; U.S. patent application Ser. No. 09/295,996, (UF-230) "Novel Peptides and the Use Thereof to Control Pests"; and U.S. patent application Ser. No. 09/295,924, (IPTL Docket No. 4137–120) "Compositions and Methods for Controlling Pests".

Materials and Methods

Chlorella Strain. Chlorella isolated from an irrigation canal near Ft. Pierce, Florida was provided by Dr. Charles Powell of the University of Florida-IFAS, Indian River Research Education and Agricultural Station, Ft. Pierce, FL. For other tranformations, Chlorella dessiccata was used.

Figure 8:
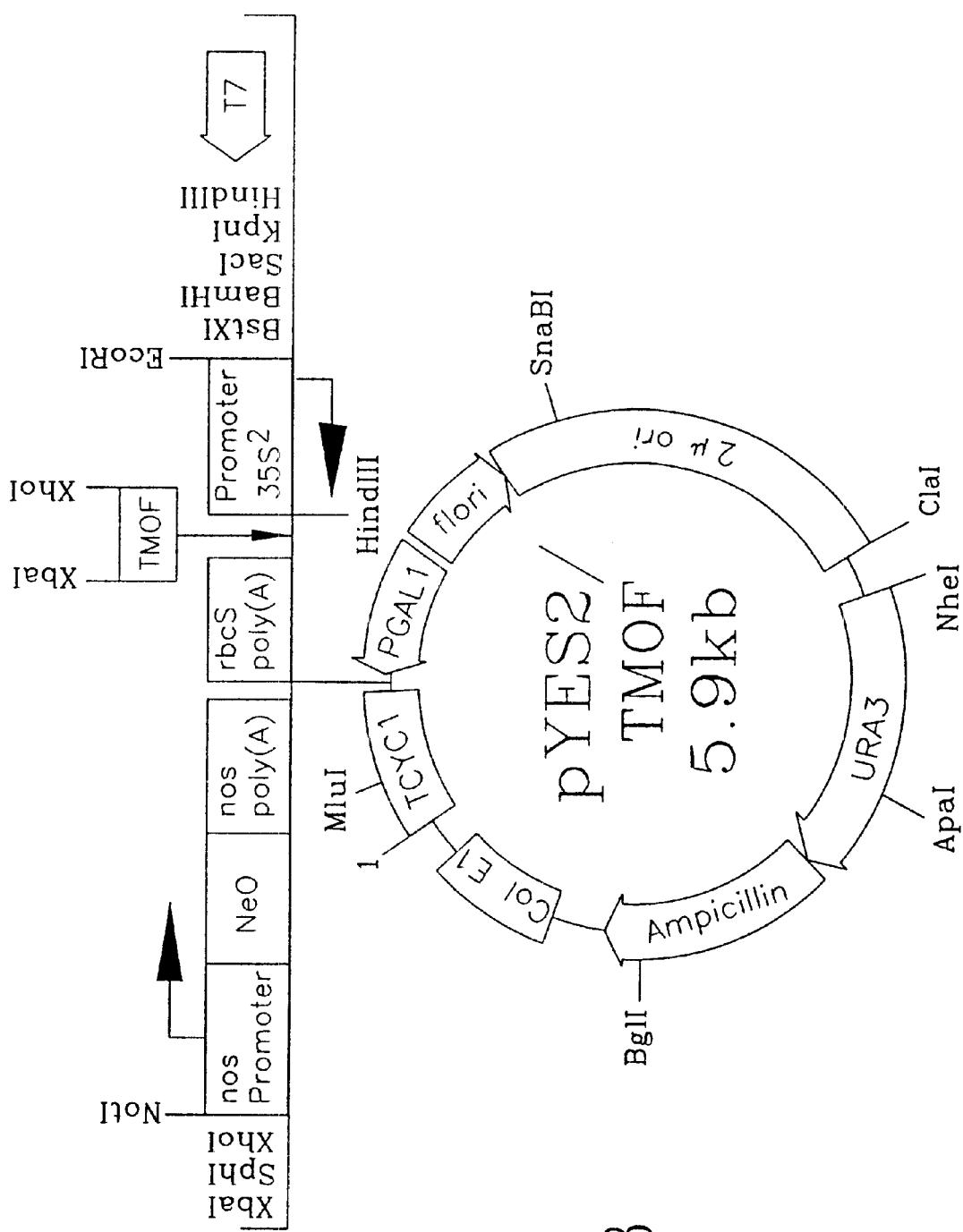
FIG. 8 shows a structure of plasmid pYES2/TMOF, including the 2 μ ori direction of replication from the $35S^2$ promoter, TMOF gene cloning site and the direction of replication of the Neomycin gene.
Figure 9:
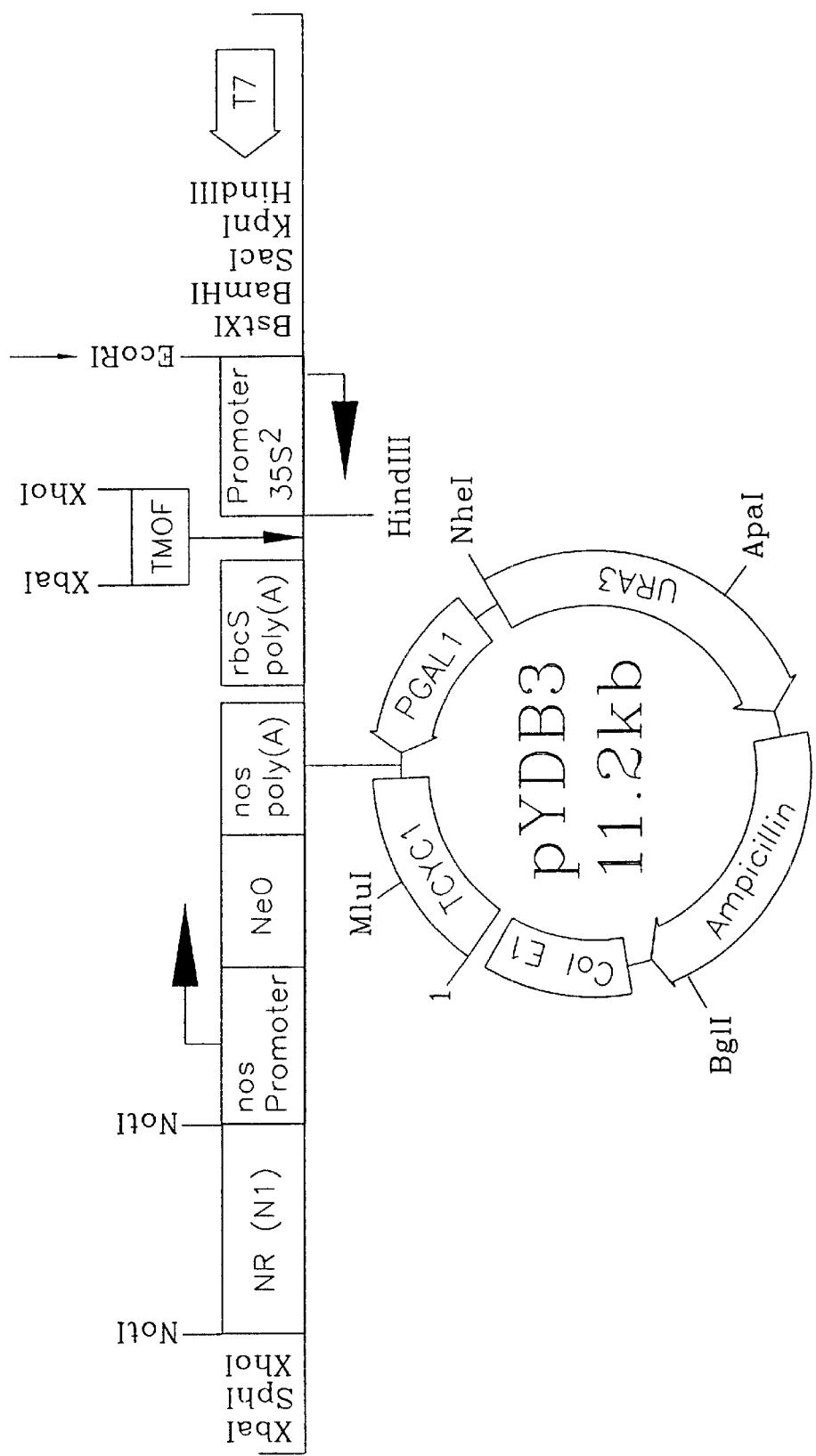
FIG. 9 shows a structure of pYDB3 including the direction of replication of TMOF from the $35S^2$ promoter, the cloning site of TMOF and the 2.3 Kb nitrate reductase gene (NR1) and the direction of replication of the Neomycin gene.
Figure 10:
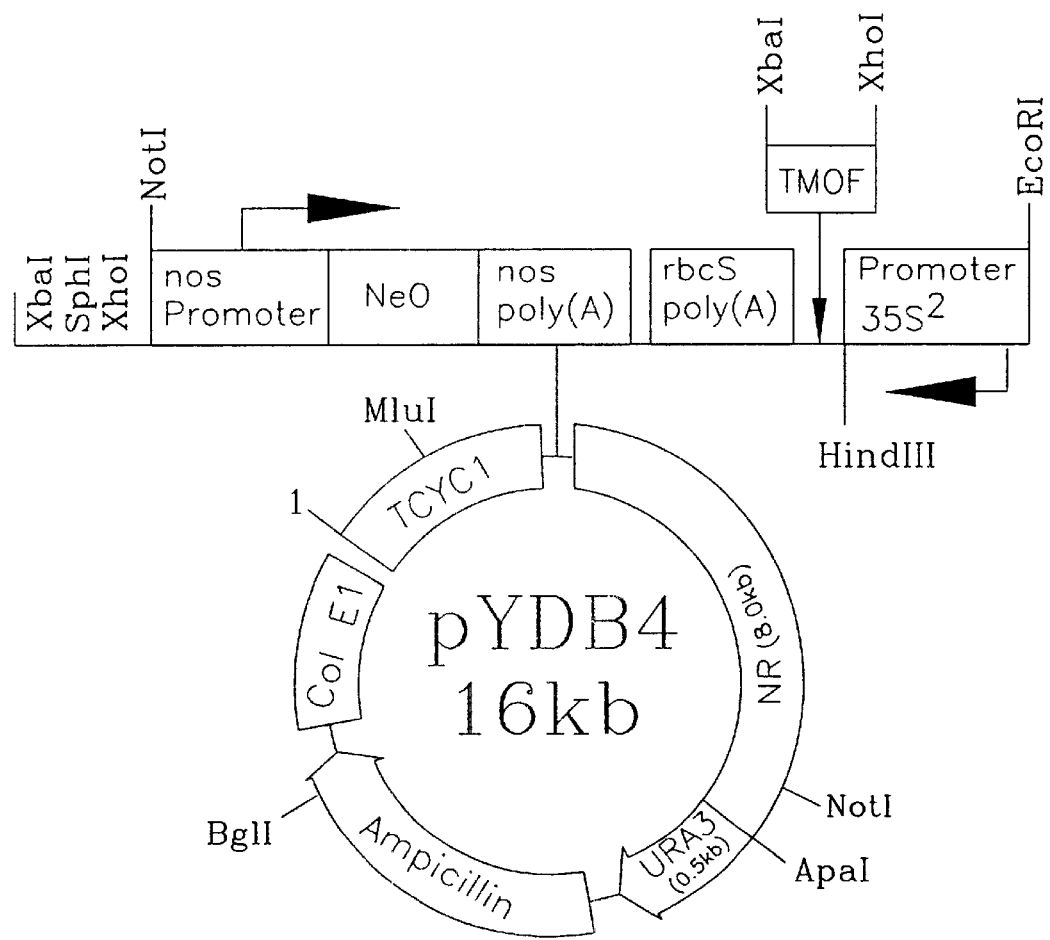
FIG. 10 shows a structure of pYDB4 including the direction of replication of TMOF gene from the $35S^2$ promoter and the direction of replication of the Neomycin resistant gene and the position of the 8.0 Kb nitrate reductase gene.

Plasmid Strain. In some procedures Chlorella was transformed with pKylx71, from Dr. Arthur Hunt of the University of Kentucky, Department of Agronomy, Lexington, Kentucky. In other procedures, transformation was achieved in the salt water Chlorella desiccata using the following plasmids that carry TMOF: pYES/TMOF, pYDB3 and pYDB4 (FIGS. 8–10).

Green Fluorescent Protein TMOF Gene. Single strand oligonucleotides primers containing the GFP and TMOF gene sequences were designed as follows:

Forward Primer:

5' AAGGTACCATGGCTAGCAAAGGAGAAGAA 3' (DB 207) (SEQ ID NO. 5)

and Backward Primer:

5' TTTCTAGATCAAGGAGGAGGAGGAGGAG-GTGCTGGAT CATATCTACCTTCGATTTTGTA-GAGCTCATCCAT 3' (DB 209) (SEQ ID NO. 6)

The forward primer carried a Kpn I restriction site, and the backward primer carried a Xba I restriction site. To bridge between the Xho I restriction site on the plasmid and the Kpn I site on the forward primer a third oligonucleotide (5' TCGAGGGTAC 3') (DB 208) (SEQ ID NO. 7) was synthesized. The GFP-TMOF gene was designed in such a way that it carried an ATG start signal and a TGA stop signal and a trypsin cleavage site sequence (IEGR). The forward and backward primers were used to amplify a GFP-TMOF dsDNA (800 bp) from 30B Cycle 3 GFP, 10 Kbp plasmid. The GFP-TMOF gene was cut with Kpn I and Xba I and directionally ligated into a pKylx71 that was cut with Xba I and Xho I, in the presence of an oligonucleotides bridge (DB 208).

Transformation of Chlorella. Chlorella cells were grown overnight, concentrated by centrifugation and incubated with 1% cellulase and 0.1% pectinase for 1 hour to partially digest the cell wall. Treated Chlorella cells were incubated with pKylx 71 GFP-TMOF plasmid in the presence of polyethylene glycol and the cells were grown on MBBM agar plates in the presence of Kanamycin (20 μg/ml) for several days at room temperature under light. Several colonies were picked with a sterile loop from each plate and transferred to tissue culture bottles containing 10 ml of MBBM media and Kanamycin and grown for several days to cell densities of $10^8$ cell/ml. Aliquots from each tissue culture were assayed for TMOF biosynthesis by ELISA (3±0.1 μg TMOF was synthesized per ml) and for larvicidal activity by adding 30 μl aliquots (90±3 ng of recombinant GFP-TMOF; $3\times10^4$ cells) into 100 μl of distilled water in microtiter plates. Each well contained a single 2nd instar larvae of Aedes aegypti. Control wells contained yeast cells or non-transformed Chlorella cells. Larval growth and mortality was checked every 24 hours under a dissecting microscope. Within 72 hours, 95% of the larvae that were fed on GFP-TMOF Chlorella died, whereas 96% and 90% of the larvae that were fed normal Chlorella and yeast cells, respectively, survived. The control larvae eventually pupated and normal adults emerged. These results demonstrate that Chlorella GFP-TMOF can be used as an effective mosquito larvicide. Because the GFP-TMOF gene did not incorporate into the Chlorella genome, the synthesis of GFP-TMOF is transient and the gene would not stay in the water long enough to induce resistance in the larvae.

Following are examples which illustrate procedures for practicing the invention. These examples should not be construed as limiting. All percentages are by weight and all solvent mixture proportions are by volume unless otherwise noted.

EXAMPLE 1

Transformation of Yeast with pYDB2

A plasmid for the transformation of yeast cells was designed and named pYDB2 (FIG. 1). The jellyfish Green Fluorescent Protein (GFP) and TMOF were cloned in tandem as a fusion protein with a trypsin cleavage site in the multiple cloning site of this plasmid (FIG. 1). The plasmid was integrated into the genome of the brewer's yeast *Saccharomyces cerevisiae* by homologous recombination and the GFP-TMOF fusion protein was expressed by the yeast.

To achieve homologous recombination of the fusion protein GFP-TMOF into the yeast genome, plasmid pYES2 (Invitrogen, CA) was modified. The Invitrogen plasmid was not designed to integrate into the yeast's genome but to express proteins as a high copy plasmid. To convert the plasmid from an autonomous replicating entity to a plasmid that can be used for homologous recombination the following changes and modifications were done:

a. The plasmid DNA was cut with two restriction enzymes NaeI at position 1007 and ClaI at position 2873 and the plasmid was recircularized and named pYDB2 (FIG. 1).

b. The multiple cloning site was then cut with two restriction enzymes XbaI and KpnI and the opened plasmid was ligated at the XbaI and KpnI restriction sites with a TMOF-GFP DNA containing a trypsin cleavage site sequence (IEGR, see FIG. 1). The new plasmid (4.9 Kb) was named pYDB2 GFP-TMOF (FIG. 1).

c. The plasmid was opened with ApaI and introduced into yeast cells with URA3 mutation using Lithium Acetate. The transformed yeast cells were grown on synthetic drop out medium lacking Uracil (SD-URA) to select for colonies that carry the URA3 gene and GFP-TMOF (FIGS. 2A and 2B).

Figure 3:
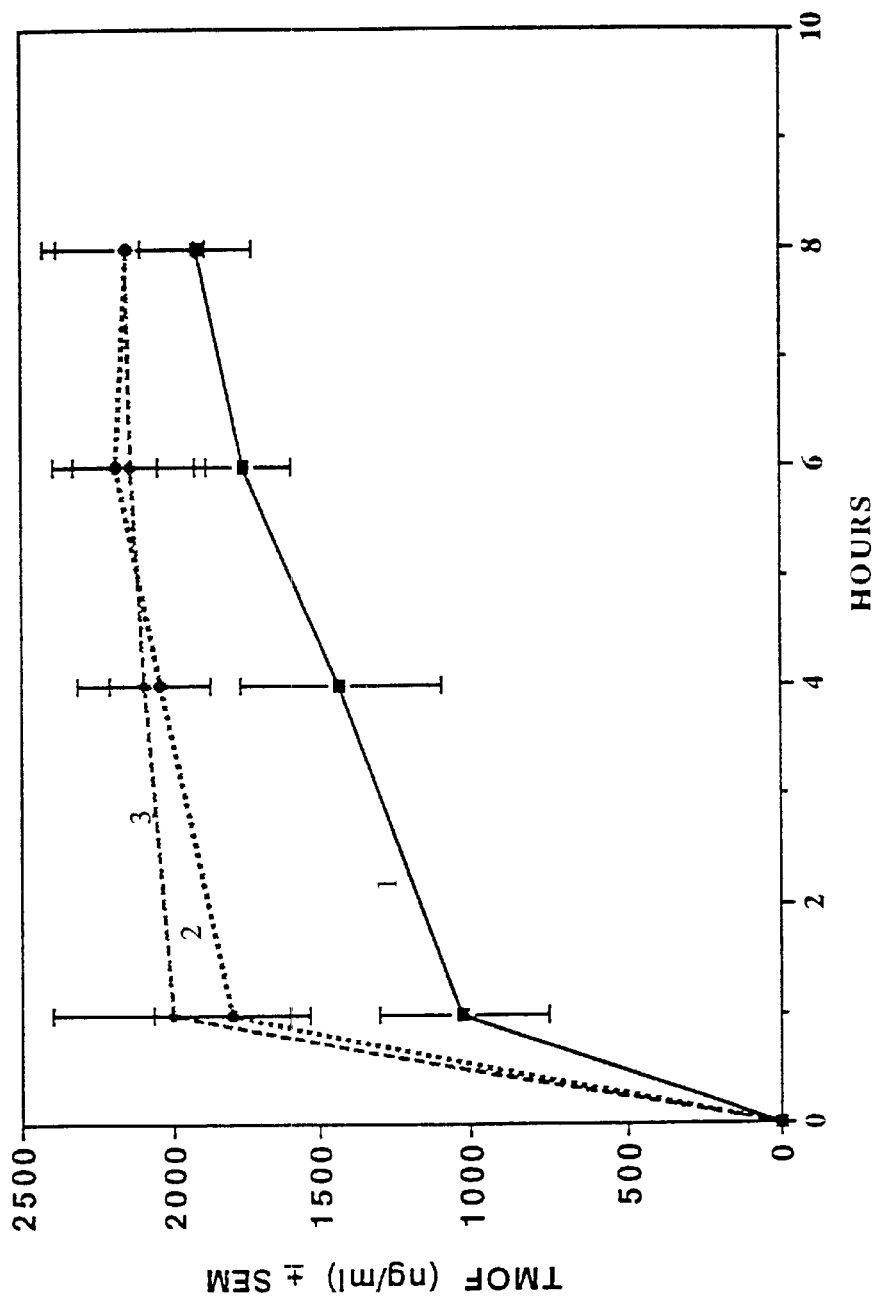
FIG. 3 shows the induction of TMOF expression (in the transformed yeast) using ELISA.

Colonies were grown on SD-URA medium for 48 hours in the presence of raffinose and induced with galactose for 1 to 8 hours. TMOF biosynthesis was analyzed by ELISA (FIG. 3) and GFP by fluorescence microscopy.

EXAMPLE 2

Control of Mosquito Larvae with Recombinant Yeast GFP-TMOF

Figure 4:
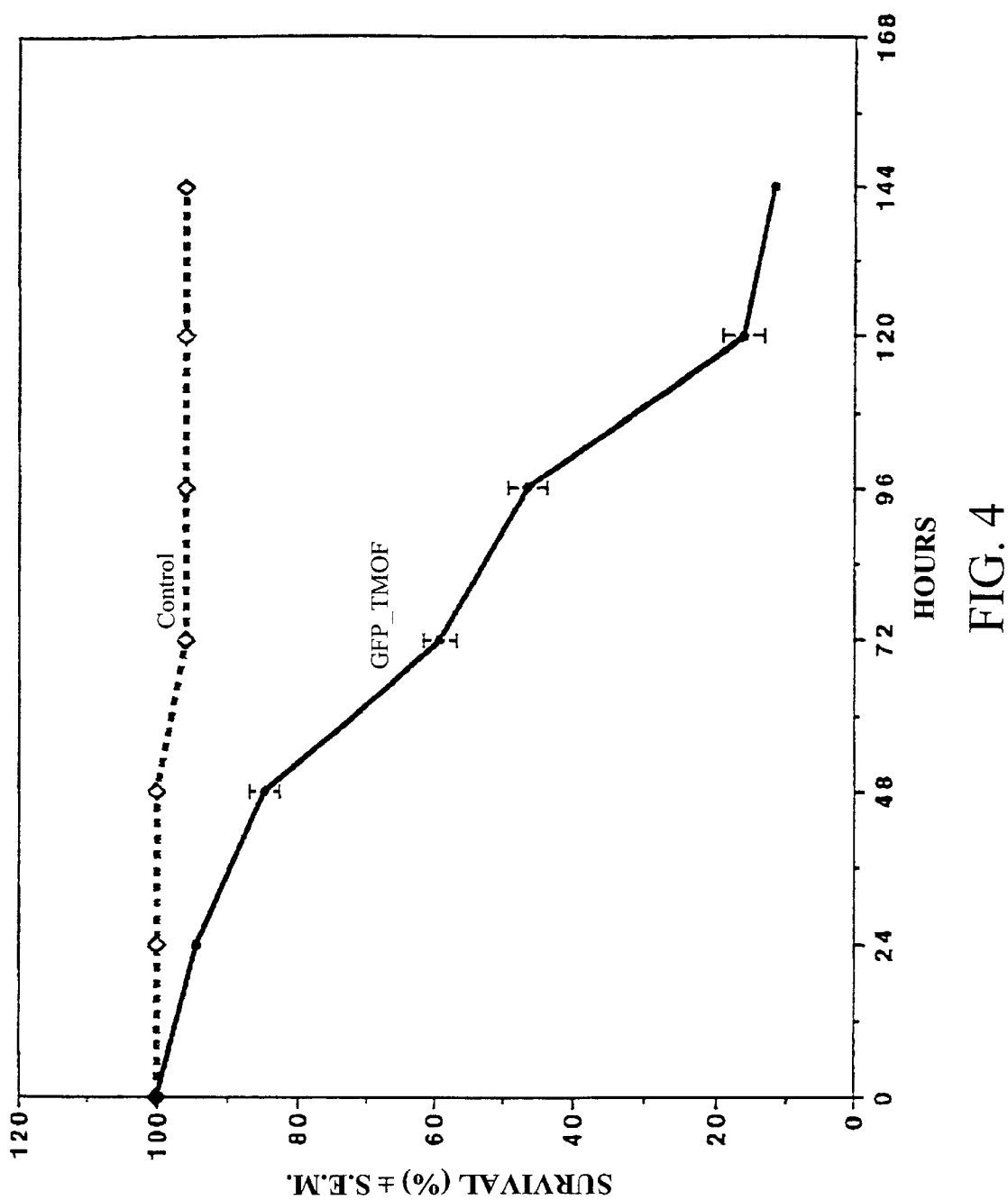
FIG. 4 shows the inhibition of *A. aegypti* larvae by ingestion of transformed yeast expressing the TMOF-GFP fusion protein. Survival of the larvae dropped to less than 20% after 144 hours. Controls exhibited no decrease in survival.
Figure 5:
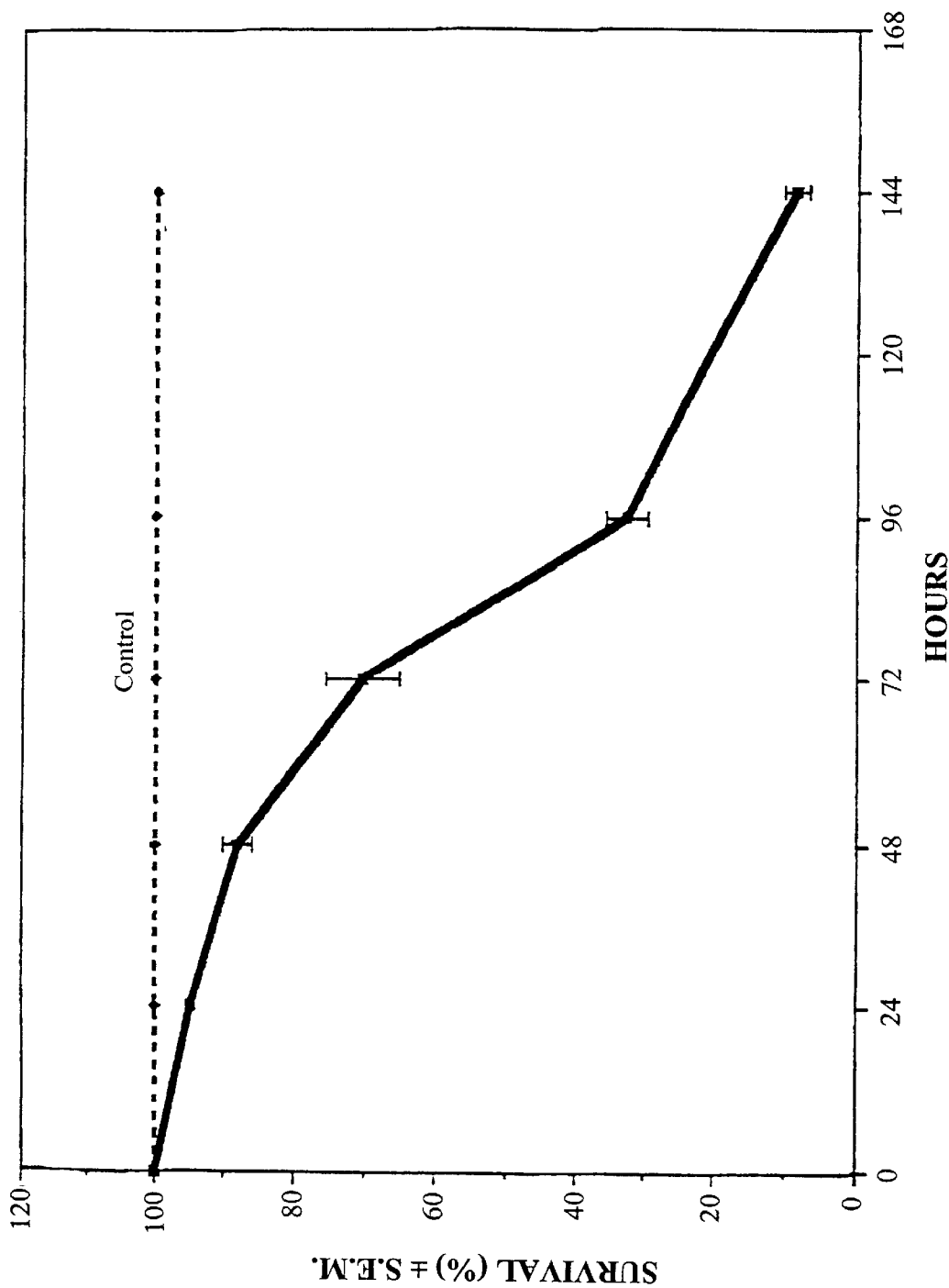
FIG. 5 shows the inhibition of *A. aegypti* larvae by ingestion of heat inactivated transformed yeast containing the TMOF-GFP gene. Survival dropped to less than 20% after 144 hours. Controls show no decrease in survival.

*Aedes aegypti* larvae were fed individually in microtiter plates containing 1.0 ml of water and $1.5 \times 10^6$ cells. At 24 hour intervals the plates were examined under a microscope and dead larvae were counted. The experiment was repeated 6 times with groups of 24 larvae using live yeast cells, or heat inactivated cells. In both cases 95% of the mosquito larvae died within 144 hours (FIGS. 4 and 5). Those larvae that did not die, did not grow. On the other hand, 100% of the controls that were fed on live yeast, or heat inactivated cells were alive and the larvae grew to the pupal stage and the newly emerged adults were normal, i.e., they took a blood meal and produced a clutch of eggs. Similar results were obtained when 20 larvae were added to containers with 100 ml of water and $6 \times 10^8$ cells. All the larvae that fed on recombinant yeast died within 6 to 7 days, whereas controls grew to the pupal stage and the adults that emerged from the pupae were normal.

EXAMPLE 3

Transformation of Chlorella with pKvlx71

Figure 6:
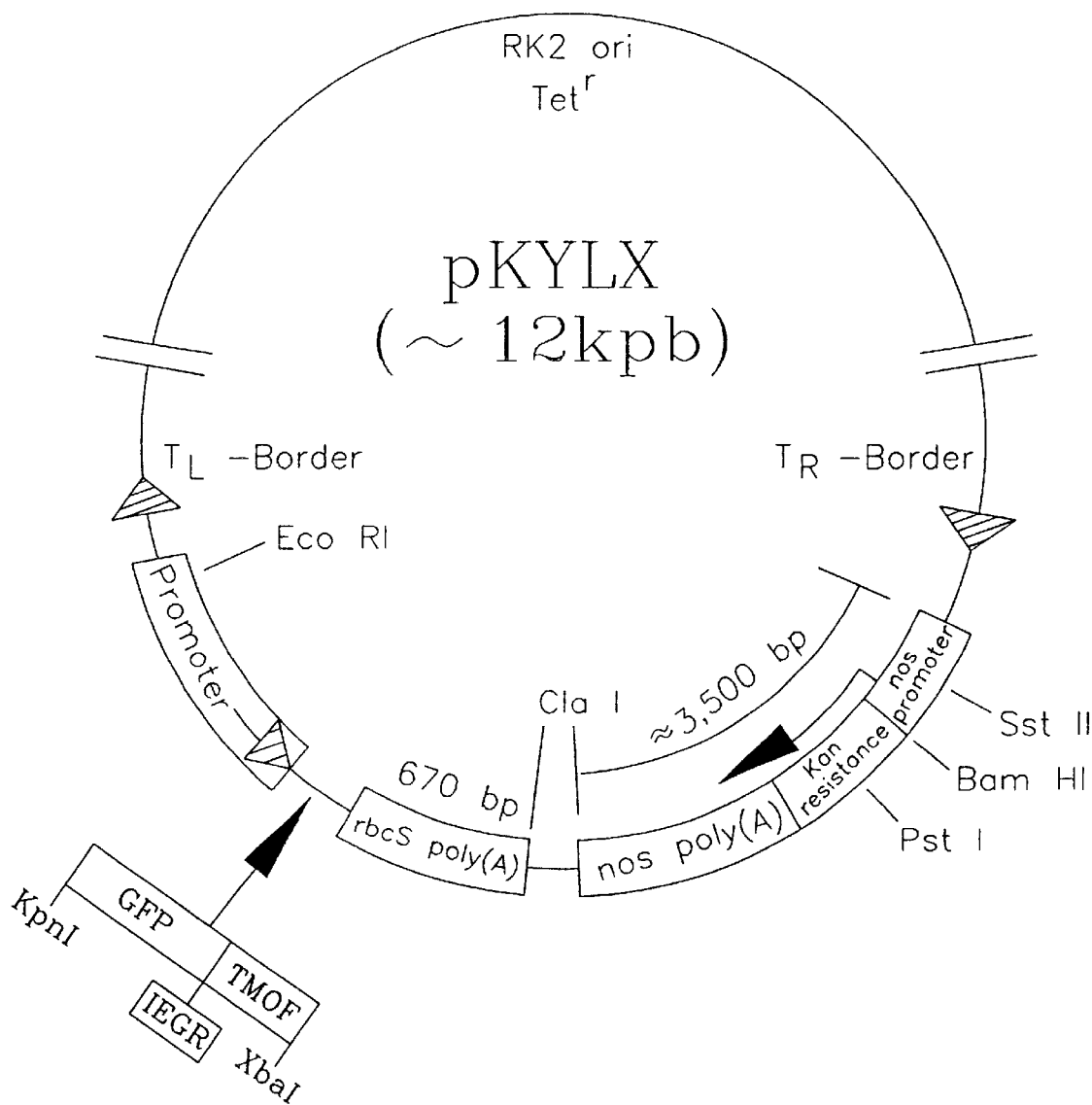
FIG. 6 depicts the pKylx71 plasmid containing the TMOF-GFP gene.

The GFP-TMOF gene from Example 1 was cloned into pKylx71 at the multiple cloning site (FIG. 6) and pKylx71 carrying GFP-TMOF was inserted into Chlorella in the presence of polyethylene glycol. Non-transformed Chlorella are not Kanamycin resistant. Transformed algae were grown on agar plates in the presence of Kanamycin to select for resistance. Single colonies were removed from the agar plate and grown in liquid media in the presence of Kanamycin and under constant light. The newly grown Chlorella cells were analyzed for GFP-TMOF synthesis by ELISA. Chlorella cells that produced TMOF were then fed to mosquito larvae.

Figure 7:
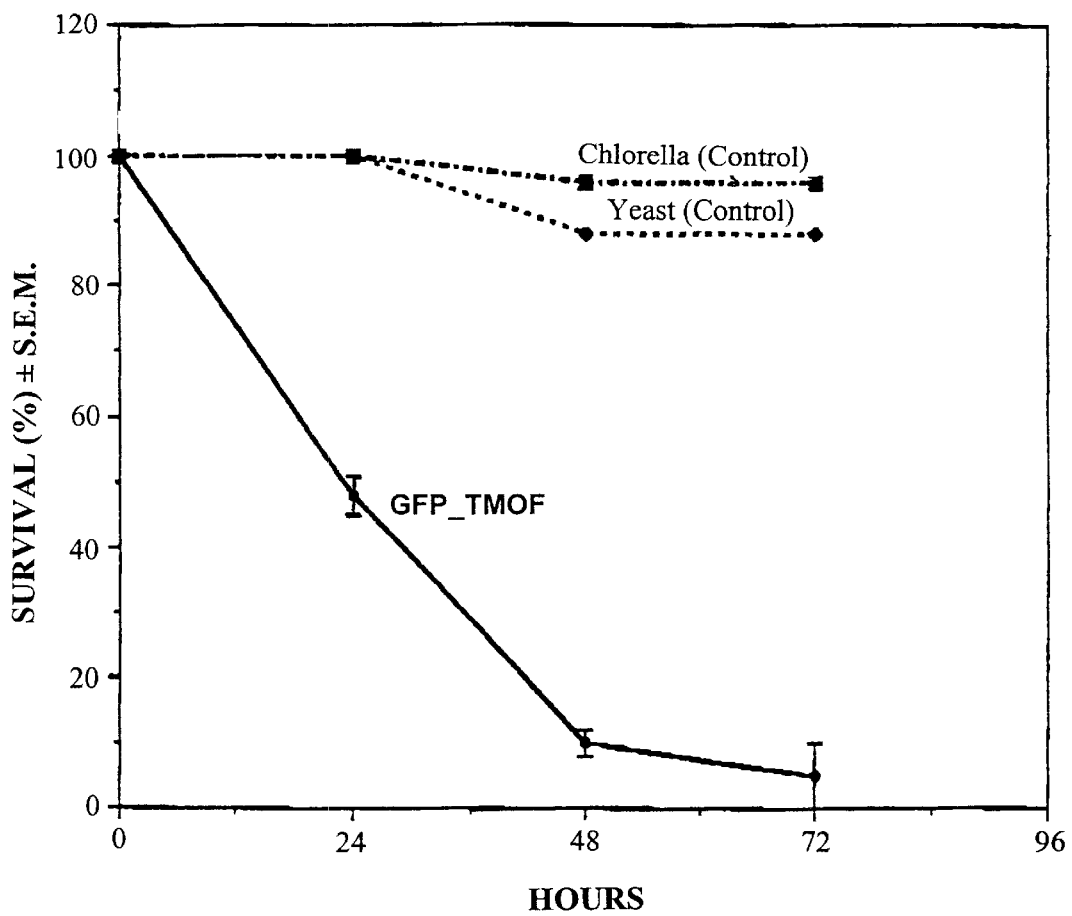
FIG. 7 shows the inhibition of *A. aegypti* larvae after ingestion of Chlorella transformed with the GFP-TMOF gene. Survival of the larvae dropped to less than 10% after 72 hours. Controls showed no significant decrease in survival rate.

Larval survival and development were compared with controls that were fed on Chlorella cells that did not produce GFP-TMOF or on normal yeast cells (FIG. 7). Ninety-five percent of the larvae that were fed on GFP-TMOF died within 3 days. Larvae that did not die did not grow and did not reach the adult stage. Larvae that were fed normal Chlorella (96%) or yeast cells (90%) developed into normal adults (FIG. 7). The use of Chlorella as the host organism for delivering the pesticidal polypeptides to mosquito larvae is advantageous since Chlorella naturally inhabit the niche occupied by mosquito larvae and are a natural food of mosquito larvae.

Chlorella is a particularly attractive vehicle for expressing TMOF for mosquito control. Chlorella is ubiquitously present worldwide and readily grows under conditions where mosquito larvae also grow. In fact, Chlorella are a natural food source for mosquito larvae. Chlorella are readily susceptible to genetic manipulation using well established cloning vectors and techniques. Furthermore, high levels of expression of cloned proteins and peptides can be obtained. Releasing the algae into the water does not upset the ecological balance because algae growth is naturally controlled by several viruses that prevent rapid growth (blooming).

EXAMPLE 4

Transformation of *Chlorella desiccata*

Although pYES/TMOF does not carry a homologous algal gene for homologous recombination, several reports in the literature indicate that the yeast 2 $\mu$ origin of replication either integrates into the genome of *Chlamydomonas reinhardtii* or causes autonomous replication in the algae (Rochaix et al., 1988). Plasmids pYDB3 and pYDB4 carry 2.3 and 8.0 Kb fragments of the nitrate reductase gene from

*Chlorella vulgaris* (Dawson et al., 1996), respectively, and were used for homologous recombination in *Chlorella desiccata*. All the plasmids express TMOF behind a strong promoter of the cauliflower Tobacco Mosaic (CaMV) $35S^2$. The TMOF synthetic gene was designed so it could be directionally cloned into pKylx 71 at the Xho I and Aba I sites. The TMOF synthetic gene carries an ATG start signal and a TGA stop signal as follows (SEQ ID NOs. 65 and 66):

```
  Xho I  Start                           Stop  XbaI
5' TCGAGATGTATGATCCAGCACCTCCTCCTCCTCCTTGAT
       CTACATACTAGGTCGTGGAGGAGGAGGAGGAGGAACTAGATC
```

The outer wall of *Chlorella desiccata* was removed with cellulase and pectinase and *Chlorella desiccata* was transformed with pYES/TMOF, pYDB3 and pYDB4 in the presence of polyethanollglycol. After transformation, algal cells were grown on artificial salt-water agar in the presence of Geneticin (600 μg/ml) to select for resistance. Non transformed *Chlorella desiccata* does not grow and dies in the presence of Geneticin (400–600 μg/ml). Single colonies were removed from the agar plate and grown in salt-water liquid media in the presence of Geneticin (400 μg/ml) and under constant light. Chlorella cells were analyzed for GFP_TMOF synthesis by ELISA. The recombinant cells synthesized about 2 to 3.7 μg of TMOF per 107 cells. Chlorella cells that produced TMOF were fed to mosquito larvae and larval survival and development was compared with controls that were fed on Chlorella cells that: a) carried the plasmids without the TMOF gene, b) cells that did not carry any plasmid, and c) normal yeast cells (Table 2).

TABLE 2

Feeding of *Aedes aegypti* larvae with recombinant *Chlorella desiccata*

| Cell type | Groups | Mortality (%) ± S.E.M. |
|---|---|---|
| a. pYES2/TMOF+ | 3 | 100 ± 0 |
| b. Yeast | 3 | 0 |
| c. pYES2/TMOF− | 3 | 0 |
| d. pKylx/TMOF+ | 3 | 100 ± 0 |
| e. pKylx/TMOF− | 3 | 0 |
| f. pYDB3 | 3 | 100 ± 0 |
| g. pYDB4 | 3 | 100 ± 0 |
| h. *Chlorella desiccata* | 3 | 7 ± 0.8 |

Groups of*Aedes aegypti* larvae (10 per group) were fed for 3–9 days with transformed and nontransformed *Chlorella desiccata* ($10^6$ cells). Controls were nontransformed Chlorella or yeast cells ($10^6$ cells). Results are an average of3 determinations±S.E.M. In a, d, f, and g 90% mortality was observed in 3 days.

The advantage of using this system is that mosquito larvae eat Chlorella in the wild and being an aquatic organism the Chlorella persists longer in the water and provides an economical means to control mosquito populations in the marsh.

EXAMPLE 5

Effect of TMOF Analogues on Mosquito Larvae

TMOF can traverse the gut epithelium, enter the hemolymph and bind a gut receptor (Borovsky, D. and F. Mahmood (1995) "Feeding the mosquito *Aedes aegypti* with TMOF and its analogs; effect on trypsin biosynthesis and egg development," *Regulatory Peptides*57:273–281; Borovsky, et al. (1994) "Characterization and localization of mosquito-gut receptors for trypsin modulating oostatic factor using complementary peptide immunochemistry" *FASEB J*. 8:350–355.). These results allowed the development of a technique by which TMOF and its analogues can directly be tested by feeding them to mosquito and other pest larvae. To find out if truncated TMOF peptides have an effect on larval growth and development, a series of peptides were synthesized and tested by feeding them to mosquito larvae at concentrations of 0 to 5.0 mg/ml (Table 3). Individual, newly hatched *Aedes aegypti* larvae were maintained in separate microtiter wells on a diet of autoclaved yeast (1 mg/ml). The diet was supplemented with TMOF peptides (Table 3). An identical number of larvae maintained on yeast served as a control. Larvae that were fed on different concentrations of TMOF peptides (0 mg/ml to 5.0 mg/ml) were monitored for eight (8) days for survival and larval growth and development. All control groups survived and larval growth and development was normal. Since larvae swallow only a small portion of the yeast particles that adsorbed the peptides, it is assumed that approximately 1 to 20 ng are taken orally at the high concentrations. These results allowed the calculation of the Lethal Dose at 50% mortality ($LD_{50}$; Table 3) of the TMOF peptides.

TABLE 3

The Effect of TMOF and its analogue peptides on mosquito larvae

| Compound | SEQ ID NO: | N | $LD_{50}$ mM ± S.E.M. |
|---|---|---|---|
| 1. $YDPAP_6$ | 11 | 3 | 0.2 ± 0.02 |
| 2. $MPDYP_5$ | 32 | 3 | >3.0 |
| 3. YDPAF | 47 | 3 | 0.33 ± 0.2 |
| 4. YEPAP | 53 | 3 | 0.35 ± 0.02 |
| 5. FDPAP | 30 | 3 | 0.37 ± 0.15 |
| 6. YDPLP | 52 | 3 | 1.5 ± 0.04 |
| 7. YDPAL | 48 | 3 | 0.52 ± 0.03 |
| 8. YAPAP | 57 | 3 | 0.54 ± 0.13 |
| 9. YNPAP | 55 | 3 | 0.55 ± 0.03 |
| 10. (D)YDPAP | 49 | 3 | 0.56 ± 0.03 |
| 11. YFPAP | 54 | 3 | 0.64 ± 0.03 |
| 12. YDPAP | 14 | 3 | 1.64 ± 0.03 |
| 13. YDLAP | 44 | 3 | 0.6 ± 0.05 |
| 14. YDFAP | 42 | 3 | 0.74 ± 0.13 |
| 15. YDAAP | 40 | 3 | 1.0 ± 0.18 |
| 16. YDPGP | 51 | 5 | 1.1 ± 0.18 |
| 17. Y(D)DPAP | 36 | 3 | 1.2 ± 0.3 |
| 18. YSPAP | 58 | 3 | 1.4 ± 0.03 |
| 19. YDPAA | 59 | 3 | 1.6 ± 0.13 |
| 20. YDPFP | 50 | 4 | 1.7 ± 0.4 |
| 21. ADPAP | 21 | 4 | 2.0 ± 0.36 |
| 22. Y(D)DP | 35 | 3 | 0.28 ± 0.01 |
| 23. DPA | 25 | 3 | 0.4 ± 0.03 |
| 24. (D)YDP | 46 | 3 | 0.51 ± 0.05 |
| 25. DAA | 23 | 3 | 0.91 ± 0.06 |
| 26. YDG | 43 | 3 | 0.95 ± 0.11 |
| 27. YDF | 41 | 3 | 0.97 ± 0.11 |
| 28. APA | 22 | 3 | 1.0 ± 0.07 |
| 29. AAP | 19 | 3 | 1.08 ± 0.07 |
| 30. YSF | 56 | 3 | 1.08 ± 0.12 |
| 31. DYP | 27 | 4 | 1.27 ± 0.17 |
| 32. YDA | 39 | 3 | 1.6 ± 0.13 |

TABLE 3-continued

The Effect of TMOF and its analogue peptides on mosquito larvae

| Compound | SEQ ID NO: | N | $LD_{50}$ mM ± S.E.M. |
|---|---|---|---|
| 33. FDP | 29 | 3 | 1.98 ± 0.6 |
| 34. YDP | 45 | 5 | 2.3 ± 0.4 |
| 35. FSP | 31 | 3 | 2.3 ± 0.13 |
| 36. YAP | 37 | 3 | 2.3 ± 0.5 |
| 37. PAA | 33 | 3 | 2.4 ± 0.34 |
| 38. PAP | 34 | 3 | 3.17 ± 0.14 |
| 39. FAP | 28 | 3 | 3.8 ± 0.23 |
| 40. ADP | 20 | 3 | >6.6 |
| 41. YD | 38 | 3 | 1.24 ± 0.06 |
| 42. DY | 26 | 3 | 3.0 ± 0.8 |

Groups of 12 to 24 mosquito larvae were incubated with different concentrations of TMOF and its analogue peptides in 100 µl microtiter plates for 7 days. Results are expressed as $LD_{50}$ ± S.E.M.

EXAMPLE 6

Control of Mosquito Larvae with Polypeptides Comprising Arginine

Individual, newly hatched *Aedes aegypti* larvae were maintained in separate microtiter wells on a diet of autoclaved yeast (1 mg/ml). The diet was supplemented with TMOF analogues (Table 4). An identical number of larvae were maintained on yeast served as a control. Larvae that were fed on different concentrations of TMOF analogues (0.5 mg/ml to 5.0 mg/ml) were monitored for 8 days for survival and larval growth and development. All control groups survived and larval growth and development were normal. Larvae that were fed TMOF analogues had increased mortality, particularly when the larvae where fed the concentrations of the analogues higher than 2 mg/ml (Table 4).

TABLE 4

Effect of Feeding TMOF-R Analogues on *Aedes aegypti* Larvae

| Compound | SEQ ID NO: | N | $LC_{50}$ (mM ± S.E.M.) |
|---|---|---|---|
| 1. YDPAP$_6$ | 11 | 3 | 0.2 ± 0.02 |
| 2. YDPAP$_6$R | 67 | 3 | 71.6>>>>> |
| 3. YDPAPR | 68 | 3 | 0.24 ± 0.02 |
| 4. YDPAFR | 69 | 3 | 0.15 ± 0.023 |
| 5. YDPAR | 70 | 3 | 0.12 ± 0.07 |
| 6. YDPR | 71 | 3 | 0.24 ± 0.026 |
| 7. DPAR | 60 | 3 | 0.46 ± 0.014 |
| 8. (DPAR)$_4$ | 61 | 3 | 0.048 ± 0.002 |

Groups of *Aedes aegypti* (12 per group) were fed TMOF and TMOF-R analogues in microtiter plates with yeast particles for 5 to 6 days. Larval mortality was checked daily. The results are the average of 3 determinations ± S.E.M.

Since larvae swallow only a small portion of the yeast particles that adsorbed the analogues it is assumed that approximately 1 to 20 ng are taken orally at the high concentrations. Using the various concentrations a lethal concentration that caused 50% mortality ($LC_{50}$) for the mosquito larvae was calculated (Table 4). The results presented in Table 4 clearly indicate that the short TMOF-R analogues are very effective, especially the (DPAR)$_4$ (SEQ ID NO. 61) polymer that is broken into 4 DPARs (SEQ ID NO. 60) in the gut.

EXAMPLE 7

Injecting TMOF-r Analogues Into *Heliothis virescens*

Individual second instar larvae of *H. virescens* were injected with TMOF-R analogues (10 to 0.25 µg per larva) and maintained in separate plastic cups on artificial diet. Twenty-four hours after the injections 3 groups of larvae (3 per group) were assayed for trypsin biosynthesis using BApNA (trypsin specific substrate; Table 5).

TABLE 5

Effect of TMOF-R analogues on trypsin biosynthesis in *Heliothis virescens*

| Compound | SEQ ID NO: | N | Amount (µg/injections) | Inhibition (% ± S.E.M.) |
|---|---|---|---|---|
| 1. YDPAP$_6$ | 11 | 3 | 10 | 56 ± 26 |
| 2. YDPAP$_6$ | 11 | 3 | 1 | 25 ± 2 |
| 3. YDPAP$_6$ | 11 | 3 | 0.5 | 11 ± 1 |
| 4. YDPAP$_6$ | 11 | 3 | 0.25 | 19.5 ± 0.7 |
| 5. YDPAPR | 68 | 3 | 10 | 53 ± 25 |
| 6. YDPAPR | 68 | 3 | 1 | 31.5 ± 2 |
| 7. YDPAPR | 68 | 3 | 0.5 | 14 ± 1 |
| 8. YDPAPR | 68 | 3 | 0.25 | 11 ± 1 |
| 9. YDPAFR | 69 | 3 | 10 | 0 ± 0 |
| 10. YDPAR | 70 | 3 | 10 | 33.5 ± 9 |
| 11. YDPAR | 70 | 3 | 1 | 39 ± 2 |
| 12. YDPAR | 70 | 3 | 0.5 | 1 ± 0.07 |
| 13. DPAR | 60 | 3 | 10 | 100 |
| 14. DPAR | 60 | 3 | 1 | 17 ± 2 |
| 15. (DPAR)$_4$ | 61 | 3 | 10 | 58 ± 36 |
| 16. (DPAR)$_4$ | 61 | 3 | 1 | 35 ± 7 |
| 17. (DPAR)$_4$ | 61 | 3 | 0.5 | 3 ± 0.3 |

Groups of *H. virescens* were injected with TMOF-R analogues in 0.5 µl of Sterile water and 24 hours later trypsin biosynthesis was followed using BApNA. Results were compared to controls that were injected with sterile distilled water and are expressed as an average of 3 determination ± S.E.M>

Trypsin biosynthesis was clearly inhibited 24 hours after injecting the TMOF-R analogues (Table 5). DPAR (SEQ ID NO. 60) at 10 µg inhibited 75% of trypsin biosynthesis, whereas TMOF caused 56% inhibition. These results indicate that TMOF-like compounds control trypsin biosynthesis in *H. virescens* as was shown in mosquito, and that these analogues can be used to control these agricultural pests.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A recombinant host transformed with a polynucleotide encoding a pesticidal polypeptide, wherein said polypeptide comprises an amino acid sequence having the general formula:

$A^1A^2A^3A^4A^5Fl$(Formula I) (SEQ ID NO. 8)

wherein:
- $A^1$ is selected from the group consisting of A, D, F, G, M, P, S and Y;
- $A^2$ is selected from the group consisting of A, D, E, F, G, N, P, S and Y;
- $A^3$ is optionally present and is selected from the group consisting of A, D, F, G, L, P, R, S and Y;
- $A^4$ is optionally present when $A^3$ is present and is selected from the group consisting of A, F, G, L, R; and Y;
- $A^5$ is optionally present when $A^4$ is present and is selected from the group consisting of A, F, L, P and R; and
- Fl is a flanking region which is optionally present and is selected from the group consisting of: P, PP, PPP, PPPP (SEQ ID NO. 9), and PPPPP (SEQ ID NO. 10);

with the proviso that the polypeptide does not consist of YDPAP$_6$(SEQ ID NO. 11), DYPAP$_6$ (SEQ ID NO. 12), PAP$_6$ (SEQ ID NO. 13), YDPAP (SEQ ID NO. 14), YDPAP2 (SEQ ID NO. 15), YDPAP$_3$ (SEQ ID NO. 16), YDPAP$_4$ (SEQ ID NO. 17), NPTNLH (SEQ ID NO. 18) or DF-OMe.

2. The transformed host, according to claim 1, wherein only $A^1$, $A^2$, $A^3$, $A^4$ and Fl are present in the formula.

3. The transformed host, according to claim 1, wherein only $A^1$, $A^2$, $A^3$ and $A^4$ are present in the formula.

4. The transformed host, according to claim 1, wherein only $A^1$, $A^2$, $A^3$ and Fl are present in the formula.

5. The transformed host, according to claim, 1, wherein only $A^1$. $A^2$ and $A^3$ are present in the formula.

6. The transformed host, according to claim 1, wherein only $A^1$, $A^2$ and Fl are present in the formula.

7. The transformed host, according to claim 1, wherein only $A^1$ and $A^2$ are present in the formula.

8. The transformed host, according to claim 1, wherein $A^1$ is selected from the group consisting of A, D, F, M and Y, and $A^2$ is selected from the group consisting of A, D, E, P and Y.

9. The transformed host, according to claim 1, wherein the polypeptide sequence comprises A, D and Y.

10. The transformed host, according to claim 1, wherein said polypeptide comprises A and D.

11. The transformed host, according to claim 1, wherein the polypeptide has from 2 to 5 amino acids.

12. The transformed host, according to claim 1, wherein the N-terminus of the polypeptide is acetylated or the C-terminus of the polypeptide is amidated, or both.

13. The transformed host, according to claim 1, wherein the C-terminus of said polypeptide is an arginine.

14. The transformed host, according to claim 1, wherein said polypeptide comprises repeating units of at least 3 amino acids wherein said repeating units are connected through at least one amino acid which is cleaved by a pest gut enzyme.

15. The transformed host, according to claim 14, wherein said repeating units are connected through an arginine.

16. The transformed host, according to claim 15, wherein said polypeptide is $(DPAR)_4$ (SEQ ID NO. 61).

17. The transformed host, according to claim 1, comprising one or more D-amino acids.

18. The transformed host, according to claim 1, which is an algae.

19. The transformed host, according to claim 1, which is a Chlorella species.

20. The transformed host, according to claim 19, wherein said Chlorella is a salt water species.

21. The transformed host, according to claim 20, wherein said chlorella is *chlorella desicata*.

22. The transformed host, according to claim 1, which is a yeast.

* * * * *

UNITED STATES PATENT AND TRADEMARK OFFICE
CERTIFICATE OF CORRECTION

PATENT NO. : 6,566,129 B1 Page 1 of 1
DATED : May 20, 2003
INVENTOR(S) : Dov Borovsky, Yaaqov Schlesinger and Sabine Maria Isidore Nauwelaers It is certified that error appears in the above-identified patent and that said Letters Patent is hereby corrected as shown below:

Column 5,
Lines 4-5, "$A^3A^4A^5$, $A^3A^4A^5Fl$, $A^4A^5$,FL,$A^5$ or $A^5FL$" should read
-- $A^3A^4A^5$, $A^3A^4A^5Fl$, $A^4A^5$, $A^4A^5Fl$, $A^5$ or $A^5Fl$ --.

Column 22,
Line 15, "pKvlx71" should read -- pKylx71 --.

Column 23,
Line 6, "Aba I" should read -- Xba I --.
Line 27, "per 107 cells" should read -- per $10^7$ cells --.

Signed and Sealed this

Twenty-fifth Day of November, 2003

JAMES E. ROGAN
*Director of the United States Patent and Trademark Office*